United States Patent [19]
Davis et al.

[11] Patent Number: 5,843,732
[45] Date of Patent: Dec. 1, 1998

[54] METHOD AND APPARATUS FOR DETERMINING CONSENSUS SECONDARY STRUCTURES FOR NUCLEIC ACID SEQUENCES

[75] Inventors: Jeffrey P. Davis; Nebojsa Janjic; Dominic A. Zichi, all of Boulder, Colo.

[73] Assignee: NeXstar Pharmaceuticals, Inc., Boulder, Colo.

[21] Appl. No.: 470,939

[22] Filed: Jun. 6, 1995

[51] Int. Cl.$^6$ .................................................. G01N 33/00
[52] U.S. Cl. ............................................................. 436/94
[58] Field of Search ................. 435/6; 536/24.3, 536/22.1; 935/77; 436/94

[56] References Cited

U.S. PATENT DOCUMENTS 5,270,163  12/1993  Gold et al. .................................... 435/6

OTHER PUBLICATIONS

Le et al., "A method for predicting common structures of homologous RNAs", Computers Biomed. Res., 28: 53–66, May 1995.
Chan et al., "A computer method for finding common base paired helices in aligned sequences: application to the analysis of random sequences", Nucleic Acids Res., 19(2): 353–358, 1991.
De Rijk et al., "DCSE, an interactive tool for sequence alignment and secondary structure research", Computer Appl. Biosci., 9(6): 735–740, 1993.
Waterman, M.S. (1988) Consensus Methods for Folding Single–Stranded Nucleic Acids, in Waterman, M.S. ed., *Mathematical Methods for DNA Sequences*, CRC Press, Boca Raton, Florida, Chapter 8, pp. 185–223.
Bartel and Szostak (1993) Science 261:1141–1148.
Beaudry and Joyce (1992) Science 257:635–641.
Bock et al. (1992) Nature 355:564–566.
Ellington and Szostak (1990) Nature 346:818–822.
Feng and Doolittle (1987) J. Mol. Evol. 25:351–360.
Gold et al. (1993) in *The RNA World*, eds., Gespeland and Atkins, Cold Spring Harbor Laboratory Press, Plainview NY, Chapter 19, 497–509.
Gutell et al. (1992) Nucleic Acids Res. 20:5785–5795.
Han and Kim (1993) Nucleic Acids Res. 21:1251–1257.
Illangasekare et al. (1995) Science 267:243–247.
Jaeger et al. (1990) Methods in Enzymology 183:281–306.
Jaeger et al. (1989) Proc. Natl. Acad. Sci. USA 86:7706–7710.
Jellinek et al. (1993) Proc. Natl. Acad. Sci. USA 90:11227–11231.
Jellinek et al. (1994) Biochemistry 33:10450–10456.
Jenison et al. (1994) Science 263:1425–1428.
Kubik et al. (1994) Nucleic Acids Res. 22:2619–2626.
Lin et al. (1994) Nucleic Acids Res. 22:5229–5234.
Pan and Uhlenbeck (1992) Nature 358:560–563.
Quigley et al. (1984) Nucleic Acids Res. 12:347–366.
Steinberg et al. (1993) Nucleic Acids Res. 21:3011–3015.
Tuerk et al. (1992) Proc. Natl. Acad. Sci. USA 89:6988–6992.
Tuerk and Gold (1990) Science 249:505–510.
Woese and Pace (1993) in *The RNA World*, eds., Gespeland and Atkins, Cold Spring Harbor Laboratory Press, Plainview, NY. Chapter 4, 91–117.
Zuker (1989) Science 244:48.

*Primary Examiner*—Nancy Degen
*Assistant Examiner*—Irem Yucel
*Attorney, Agent, or Firm*—Swanson & Bratschun LLC

[57] ABSTRACT

An interactive computer program generates a composite dot matrix representation of secondary structure elements from a set of functionally related oligonucleotides. The composite image facilitates visual detection of conserved secondary structure motifs with similar sequence sets. The complete pattern displaying all possible base pairings can be readily pruned with two progressive filters to provide the user with a simplified figure displaying only the most stable and conserved regions. Additional simplification of the structure matrix image can be achieved by eliminating mutually exclusive structures. Alignment editing provided within the program facilitates refinement of the consensus secondary structure.

20 Claims, 16 Drawing Sheets
(7 of 16 Drawing Sheets(s) Filed in Color)

```
GGGAGCUCAGAAUAAACGCUCAAGGGUUGU              GACAAGUACACCUGCGUCUUCGACAUGAGGCCCGGAUCCGGC
GGGAGCUCAGAAUAAACGCUCAAGGGGGCAAGGCUACA      GACAAGUGCACCAACUUCGACAUUCGACAUGAGGCCCGGAUCCGGC
GGGAGCUCAGAAUAAACGCUCAACGUCAGAAGGCAACGUA UA GGCAAGCACACAGCAUUCGACAUGAGGCCCGGAUCCGGC
GGGAGCUCAGAAUAAACGCUCAACCUCUCGAAGACAACGCUGU GACAAG ACA UUCGACAUGAGGCCCGGAUCCGGC
GGGAGCUCAGAAUAAACGCUCACAAAGUGGGAAACGCUACUUGACAAG  ACACCACUUCGACAUUCGACAUGAGGCCCGGAUCCGGC
GGGAGCUCAGAAUAAACGCUCAAGGCUACGCUAAU         GACAAGUGCACUUGGGUUCGACAUGAGGCCCGGAUCCGGC
GGGAGAUGCCUGUCGAGCAUGCUGCUCUGGUAACGCAAU     GUCAAGUGCACAUGAGUAGCUAAACAGCUUUGUCGACGGG
GGGAGAUGCCUGUCGAGCCUGCUGAGCCGCAGGUAACGGACC  GGCGAGAUGCACCAUUGUAGCUAAACAGCUUUGUCGACGGG
GGGAGAUGCCUGUCGAGCAUGCUUCGGCGCUUCGACAUGA    GACAAGUGCAGUAGCUAAACAGCUUUGUCGACGGG
GGGAGAUGCCUGUCGAGCAUGCUGAAGGGGAAACGUUGA     GUCCGGUACACCCUGGUAGCUAAACAGCUUUGUCGACGGG
GGGAGAUGCCUGUCGAGCAUGCUGAGCAUGCGGUAACGGUA C GACAAGACCACUCCAACUGUAGCUAAACAGCUUUGUCGACGGG
GGGAGAUGCCUGUCGAGCAUGCUGAGCAUGCUGAGGGUAACGCUGA GUCAAGUGCACUCGACAUGUAGCUAAACAGCUUUGUCGACGGG
GGGAGAUGCCUGUCGAGCAUGCUGAGCAUGCUGGGGAAACGCUAUC GACGAGUGCACCCGGCAGUAGCUAAACAGCUUUGUCGACGGG
GGGAGAUGCCUGUCGAGCAUGCUGUGUCCGAGGGUAACGCUUGG    GUCAAGCACACCUCGUAGCUAAACAGCUUUGUCGACGGG
GGGAGAUGCCUGUCGAGCAUGCUGAGCAUGCUGUCGGGGUAACGCUAUU GGCAAGG CACCCGACCAGCUGCGUAGCUAAACAGCUUUGUCGACGGG
GGGAGAUGCCUGUCGAGCAUGCUGAGCAUGCUGAGGGGUAACGCUGUGGACAAGUGCACCUGCGUAGCUAAACAGCUUUGUCGACGGG
GGGAGAUGCCUGUCGAGCAUGCUGAGCAUGCUGAGCUGGUAACGCUACU GACAAGCUCACCUCAGUAGCUAAACAGCUUUGUCGACGGG
GGGAGAUGCCUGUCGAGCAUGCUGAGCAUGCUGAGGUAACGCUAUA    GUCAAG ACACCCCGGCACCCCGUAGCUAAACAGCUUUGUCGACGGG
GGGAGAUGCCUGUCGAGCAUGCUGAGCAUGCUGAGGGGUAACGCAUU   GGCAAG ACACCCAGCCCCGUAGCUAAACAGCUUUGUCGACGGG
GGGAGAUGCCUGUCGAGCAUGCUGAGCAUGCUGGGGAGAAACGUACC   GUCGAGC CACUCCAUGCGUAGCUAAACAGCUUUGUCGACGGG
GGGAGAUGCCUGUCGAGCAUGCUGCACAGGCUGGGGUAACGCUGU     GACAAGAUCACCCCAGUUUGGUAGCUAAACAGCUUUGUCGACGGG
GGGAGAUGCCUGUCGAGCAUGCUGAGCAUGCUGGGGCAACAGGCUGCU  GACAAGUGCACCUGUAGCUAAACAGCUUUGUCGACGGG
```

Fig. 4

UGACUCGAACCCUUGGAAGACCUGAGUACAGGUAUACCAGuucga
  cgcucaaUCCUUGGAAGCCG    UA   CGGAUACCAAUUGAGUGGCCAUAUG
UAUCGAGUGGCCUUGGCAGACCAGGCCC   GGUAUACCACCA
CGAGAUUCAACCUUGGAAGUCA    AUCG   UGAAUACCAUUGUU UCAAGAAUUCCGUUUUCAGU CGGGAAAAACUGAACAA
GAAUAUCUUCCGAA GCCGAACGGGAAAACCGGCAUCU
UCAAGGUUUCCGAAAGAAAU CGGGAAAACUGUCU
AGUAGAUAUCCGAA GCUCAACGGGAUAAUGAGCAUCU
AGAUAUGAUCCGUAAGAGGA CGGGAUAAACCUCAAC
GUCAUAUUACCGUUACUCCU CGGGAUAAGGAGAUCU
AGGAAUCGACCCAAGCCAAA GGGGAUAAUGCGGCAUC
AGUAAUGACCAGAGGCCCAA CUGG UAAACGGGCGGUC

```
GAAUGAAUGUGAUGAACAGGUGUCGGGGUGGAU GGGUGG
GGAAUGAAUGUGAUGAACAGGUGUCGGGGUGGAU GGGUGG
AGAAUGAAUGUGAUGAACAGGUGUCGGGGUGGAU GGGUGG
 CGCCUUAGUCGCCAUAAUGCUGUCGGGGUGGAUA GGGUGG
 GACGCGUGCUGGCCUCGACCGUGUGGGUGCGGAU GGGUGG
```

METHOD AND APPARATUS FOR DETERMINING CONSENSUS SECONDARY STRUCTURES FOR NUCLEIC ACID SEQUENCES

BACKGROUND OF THE INVENTION

1. Technical Field

The present invention is directed toward identifying structural similarities between functionally related oligonucleotides, and more particularly toward identifying consensus secondary structures for functionally related oligonucleotide sequences.

2. Background Art

Randomized oligonucleotide libraries contain molecules with a wide spectrum of potential functional properties. High-efficiency screening of these libraries, by use of the SELEX (Systematic Evolution of Ligands by EXponential enrichment) process has recently led to identification of oligonucleotides with unique binding and catalytic features. See e.g. Tuerk and Gold (1990) Science 249:505–510 and Illangasekare et al. (1995) Science 267:243–247. In most SELEX process experiments, interim rounds of selection-amplification are carried out until the majority of molecules in the enriched pool share the functional property for which they were selected. In a typical successful SELEX process experiment, cloning and sequencing of molecules from the enriched pool results in a collection of sequences. As a consequence of the functional relatedness among the clones, these molecules can typically be classified into families based upon similar primary structure. See e.g. Feng and Doolittle (1987) J. Mol. Evol. 25:351–360, which is incorporated by reference herein. Functional relatedness also implies that a secondary structural motif may be common to members of a family.

While basic elements of the consensus primary structure in a similar sequence set are recognized either by inspection or with the use of multiple sequence algorithms such as those disclosed by Feng and Doolittle, supra, recognition of conserved secondary elements is often problematic, especially in a large data set. The search for a common secondary structural motif is often complicated by the existence of many individual sequences that can assume a multitude of mutually exclusive secondary structures with similar predicted free energies of folding. Some groups of conformations will exist in rapid equilibrium with one another and some will be kineticly trapped. A complex function of thermodynamic stability and kinetics of folding and conformational interconversion determines the overall conformational repertoire of any given sequence. During identification of oligonucleotides having select functional properties using the SELEX process, molecules in which the most populated solution conformer coincides with the active conformation have a selection advantage over those in which competing, inactive conformations predominate. However, molecules in which inactive conformations predominate can still be selected efficiently as long as the active conformation is accessible. It is therefore extremely difficult to deduce the active conformation by examining only the most thermodynamically stable set of conformations for any one sequence. A set of similar sequences is considerably more informative, since the active conformation must be accessible and shared by all members, while alternative secondary structures will occur more randomly. Analyzing a set of sequences by examining optimal and suboptimal folding from a Zuker-Turner secondary structure prediction program (Jaeger et al. (1989) Proc. Natl. Acad. Sci. USA 86:7706–7710; Jaeger et al. (1990) Methods in Enzymology 183:281–306) rarely results in identification of a common secondary structure. In addition, such a scheme will not identify certain well known structural motifs such as pseudoknots and G-quartets which have been found in sequence sets identified by SELEX process experiments.

In an effort to identify secondary structures for a single sequence of oligonucleotides, dot matrix representations have been used. See Quigley et al. (1984) Nucleic Acid Res. 12:347–366, the contents being incorporated by reference herein. In this previous method rows and columns of a structure matrix, M, represent an oligonucleotide sequence written in a 5' to 3' direction. A dot is placed on an individual matrix element $M_{ij}$ if base i and j are potential Watson-Crick base pairs. Double helical (stem) regions are then recognized as runs of sequential dots perpendicular to the diagonal.

The utility of the dot matrix representation disclosed by Quigley et al., supra, is limited to determining secondary structure of a single oligonucleotide sequence. This method has been of no use in determining the consensus secondary structure motif for a plurality of functionally related oligonucleotides.

SUMMARY OF THE INVENTION

The present invention utilizes a dot matrix display to visualize consensus secondary structures of functionally related sequence sets. The functionally related sequence sets are screened from an oligonucleotide library to identify a plurality of oligonucleotides having a select functional property. The identified plurality of oligonucleotides are then analyzed to identify a nucleotide sequence for each oligonucleotide. The oligonucleotides are then aligned according to primary structural similarity. A matrix representing the relative strength of a select property between nucleotides of each aligned oligonucleotide sequence is then constructed. The matrix representing the relative strength of the select property is analyzed to identify high-strength consensus structures. This information is then translated to a consensus secondary structure.

The matrix is preferably constructed through the use of a digital computer. The visual display of the matrix representing relative strength of the select property is preferably accomplished by means of a color monitor (relative strength being indicated by select colors). Interactive features are provided for editing the overall sequence alignment, display editing that allows progressive filtering or pruning of the display from complex (all inclusive) to simpler (showing only the most conserved and most stable regions), easy identification of mutually exclusive structures, detection of base pairing covariation and detection of G-quartet structures.

Another embodiment of the present invention is a computer system including a central processing unit and an associated memory. The computer system includes means for inputting into the associated memory a plurality of functionally related oligonucleotide sequences aligned according to primary structure similarity. The processor is programmed to compute a matrix representing the relative strengths of base pairing between nucleotides of each aligned oligonucleotide sequence in the memory. A programmed filter identifies consensus stem structures of a select strength from the computed matrix. The system preferably includes code enabling varying of the alignment of the plurality of functionally related oligonucleotide sequences.

Another embodiment of the present invention is an application program for identifying consensus secondary structures for a plurality of nucleic acid sequences having select functional properties, the application program stored on machine readable media. The application program includes a routine for inputting into the associated memory a select plurality of functionally related oligonucleotide sequences. An additional routine instructs the central processing unit to compute a matrix representing the relative strength of a select property between nucleotides of each aligned oligonucleotide sequence in the memory. An identifying routine instructs the central processing unit to identify consensus stem structures having select property strands from the computed matrix.

The method and apparatus of the present invention enable researchers to quickly identify consensus secondary structure for a plurality of functionally related oligonucleotides. The present invention therefore provides researchers a powerful test for identifying common structural elements resulting in the functional attributes of a set of oligonucleotides, which information can in turn assist researchers in identifying and developing helpful pharmaceuticals.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 4 (SEQ ID NO: 1–SEQ ID NO: 22) is a family of sequence sets of ligands which bind to bFGF;

DETAILED DESCRIPTION OF THE PREFERRED EMBODIMENT

As an initial step, functionally related oligonucleotides must be isolated using, for example, the SELEX process as described in Tuerk and Gold, supra, Illagnsekare et al., supra, and Gold et al. U.S. Pat. No. 5,270,163, each of which is incorporated by reference herein. The oligonucleotide sequences are then arranged in sets aligned according to primary structure similarity using, for example, the multiple sequence alignment algorithm disclosed in Feng and Doolittle, supra. In SELEX process experiments the random oligonucleotide region is flanked with defined (fixed) sequence regions which are required for amplification by the polymerase chain reaction. Only the evolved (initially random) regions are considered in alignment but the fixed regions are reintroduced prior to generation of the secondary structure matrix.

Figure 1A:
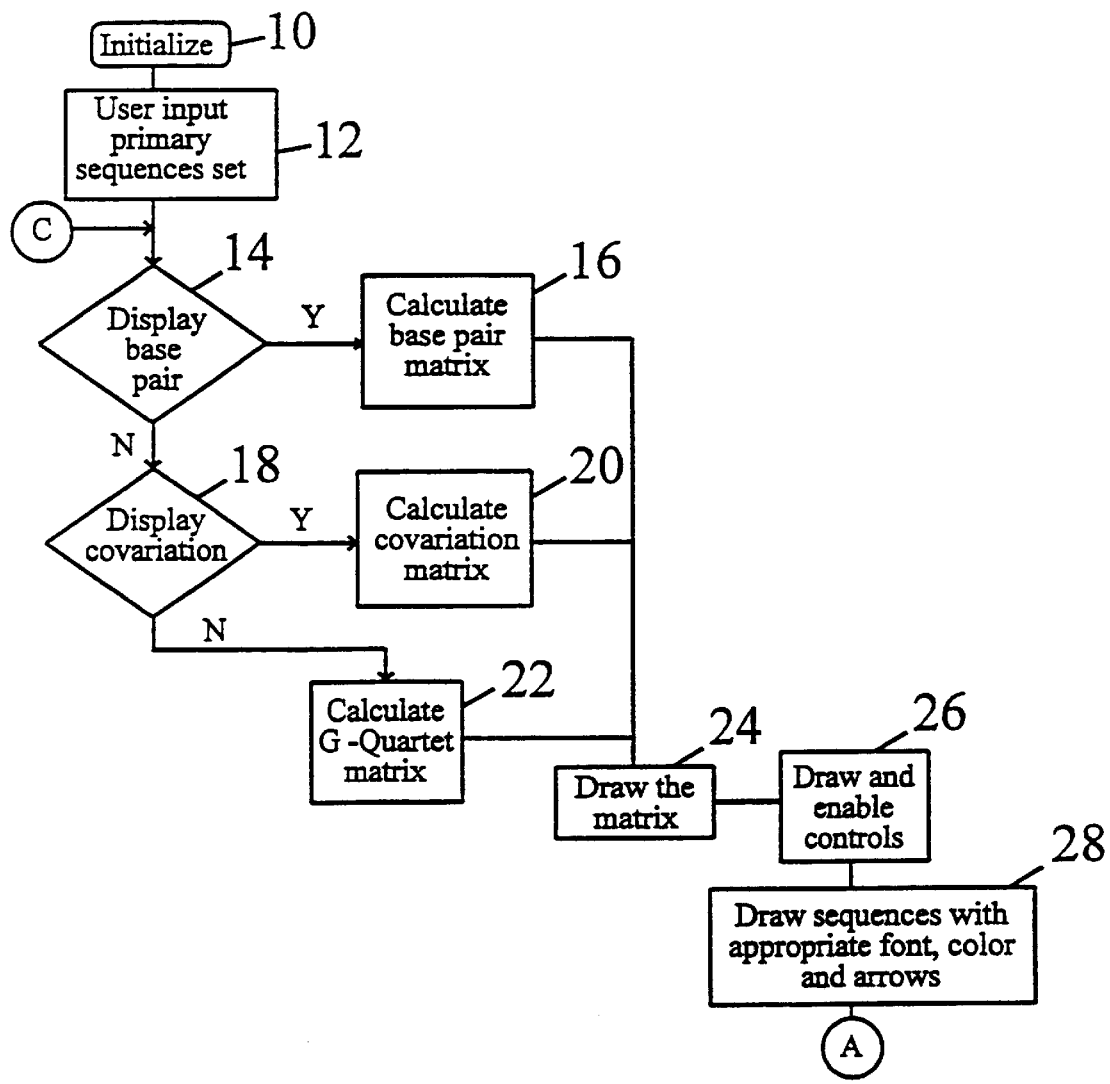
FIGS. 1A–1C are a flow diagram of a computer program for use in determining consensus secondary structures for nucleic acid sequences in accordance with the present invention.
Figure 1B:
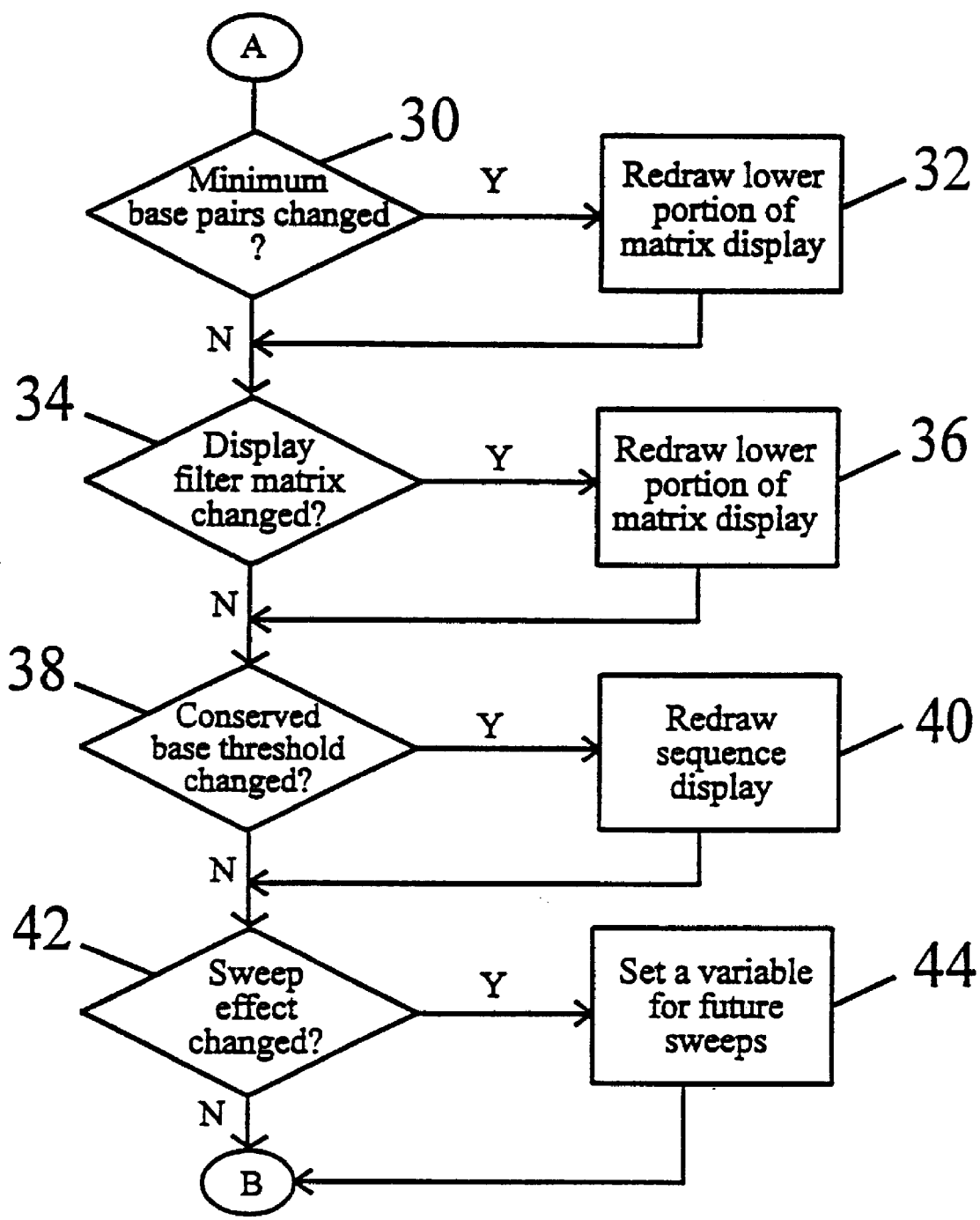
Figure 1C:
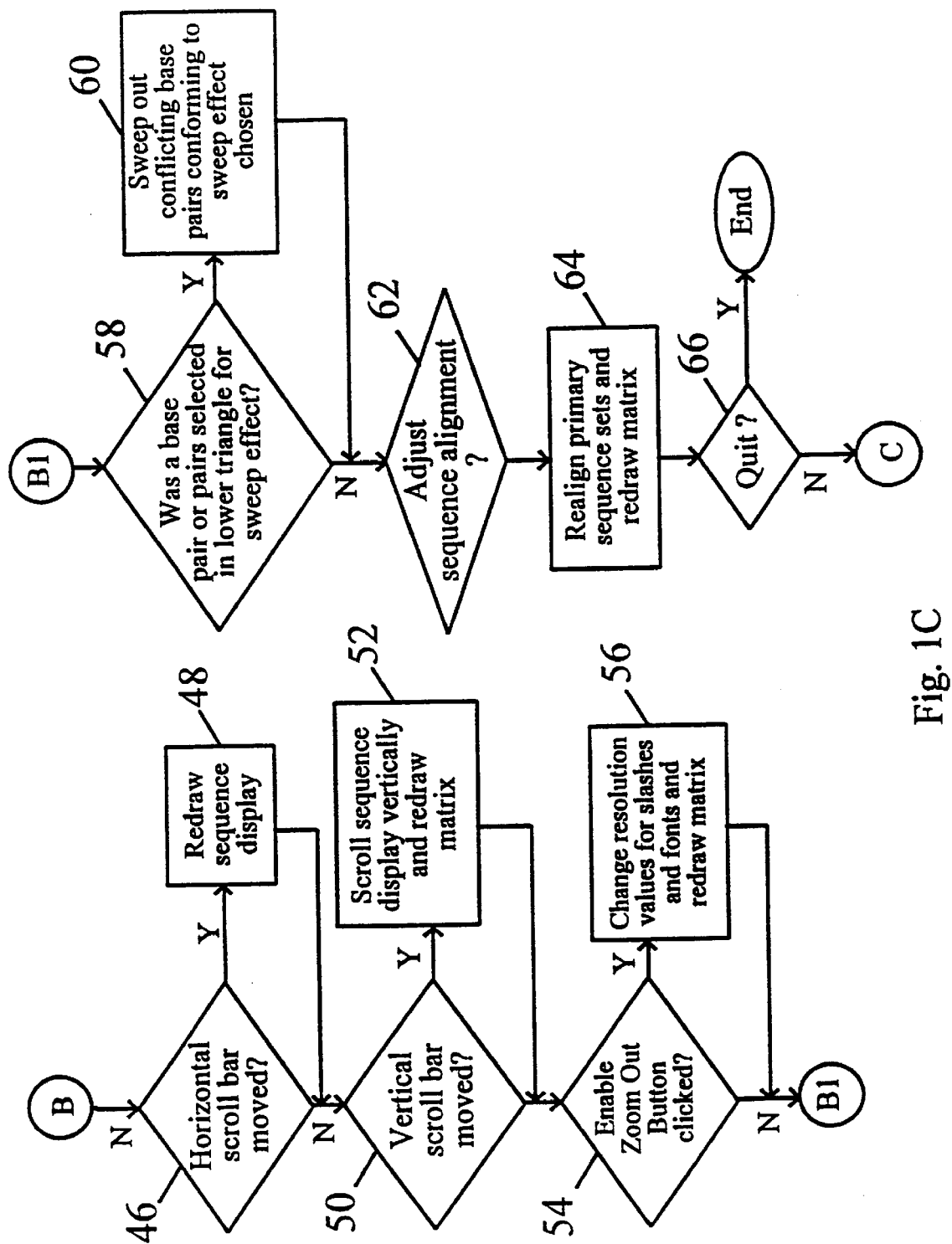

FIGS. 1A–1C are a flow chart illustrating the logic of a computer program of the present invention for identifying consensus secondary structures. At block 10 the central processing unit or processor is initialized, which includes initializing graphics port, fonts, windows, menus, text editing, displays and loading menus and cursers. At block 12 a user inputs an aligned set of oligonucleotide sequences derived as discussed above. At decision block 14 it is determined whether a user has selected display of the base pair matrix. If the user has made such a request, at block 16 the structure matrix for expanded Watson-Crick base pairing (standard Watson-Crick, including G-U wobble base pairs) is calculated according to Equation 1 below:

$$M_{ij}=1/N\Sigma_n\Sigma_{b:b'}C(b:b')\delta(a_{n,i}-b)\ \delta(a_{n,j}-b') \qquad (1)$$

Figure 2:
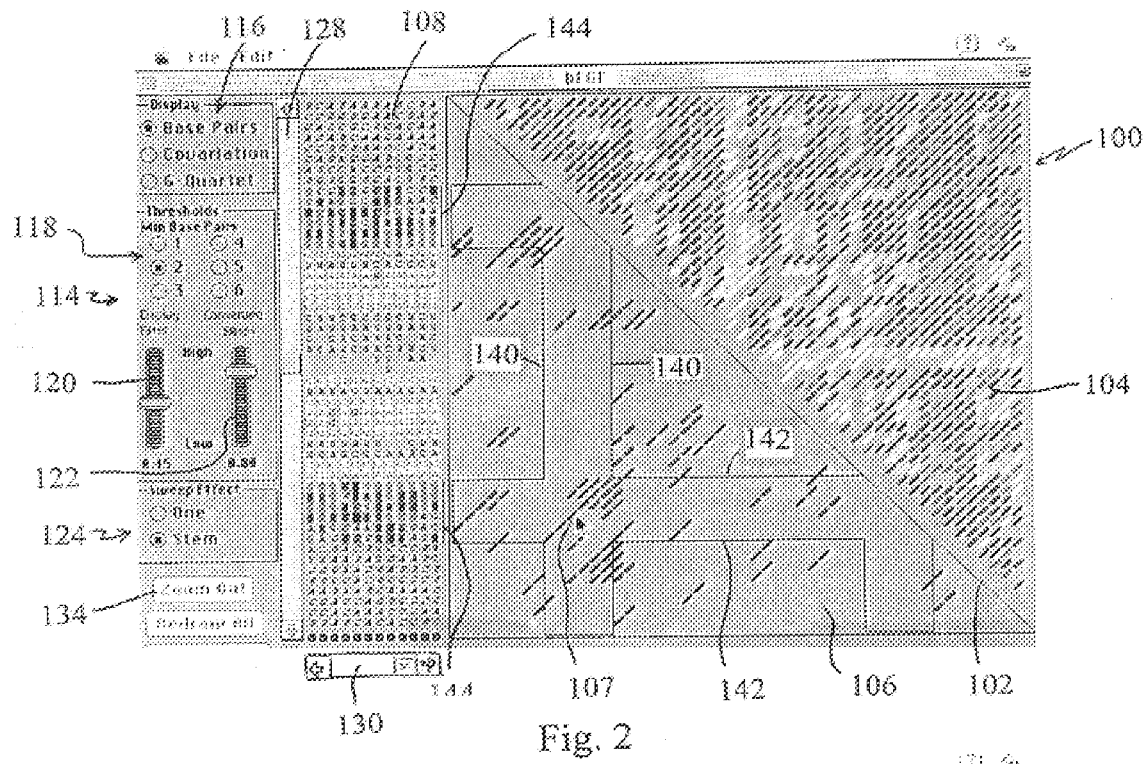
FIGS. 2 and 3 illustrate a screen display of the base pair matrix for determining consensus secondary structures for nucleic acid sequences in accordance with the present invention and includes various controls and filters in accordance with the present invention.

$a_{n,i}$ designates the nucleotide at position i of sequence n in the N-sequence multiple alignment, b:b' indicate one of the four Watson-Crick or two G:U base pairs, C(b:b') is a general coefficient which can, for example, reflect the energy of base pair formation, and $\delta(a_{n,i}-b)$ is the Kronecker delta function, which is equal to 1 if $a_{n,i}$=b, and is otherwise equal to 0. A minimum length hairpin loop is imposed to be two nucleotides long, so all diagonal elements within two positions of the main diagonal are set to 0. In the preferred embodiment described herein, C(b:b') =1 for all base pairs of b:b', so $M_{ij}$ varies from 0 indicating no base pair formation between positions i and j in any of the N sequences to 1 indicating that all sequences form a base pair between positions i and j. For this definition of M, the consensus matrix simply represents the degree to which base paring is conserved within a set of similar sequences. A sample display of a base pair matrix 100 is illustrated in FIG. 2.

If at decision block 14 display of base pairing is not selected, at block 18 it is determined whether the user has selected display covariation. If so, at block 20 the covariation matrix is calculated. Base pairing covariation determines the change in concert at two positions in a sequence according to Watson-Crick (or expanded Watson-Crick) rules. Base pairing covariation has been demonstrated to be of substantial value for predicting secondary structures. See Gutell et al., supra. A structure matrix representing base paring covariation is determined by the following formula:

$$M_{ij} = \frac{1}{2}(\Sigma_{b:b'} f_{bi,b'j} \log_2 [f_{bi,b'j}/f_{bi}f_{b'j}]) \quad (2)$$

where $$f_{bi} = 1/N \Sigma_n \delta(a_{n,i} - b)$$

and $$f_{bi,b'j} = 1/N \Sigma_n \delta(a_{n,i} - b) \delta(a_{n,j} - b')$$

The $f_{bi}$ term is the fraction of sequences which have a base b at position i in the multiple alignment and $f_{bi, b'j}$ is the fraction of sequences which form a b:b' base pair at positions i and j. Here, complete covariation of expanded Watson-Crick base pairs at positions i and j result in $M_{ij}=1$, while either no base pairing or no covariation of the structure at position i and j result in $M_{ij}=0$. Intermediate values of $M_{ij}$ are possible for cases where less than complete covariation is observed. While the preferred embodiment disclosed herein limits the covariation analysis to expanded Watson-Crick base pairs, extending this analysis to include covariation of other types could be readily accomplished by one skilled in the art.

If at decision block 18 it is determined that display covariation was not elected by a user, the program continues with calculation of a G-quartet matrix at Block 22. The G-quartet matrix is calculated using the following equation:

$$M_{ij} = 1/N \Sigma_n [\delta(a_{n,i} - G) \delta(a_{n,j} - G) \times \theta(\delta(a_{n,i+1} - G) \delta(a_{n,j-1} - G) + \delta(a_{n,j-1} - G) + \delta(a_{n,j+1} - G))] \quad (3)$$

$\theta(x)$ is the Heaviside step function, equal to 1 for x>0 and zero otherwise. In the preferred embodiment, $M_{ij}$ is the fraction of potential G:G quadruplex base pairs that is bracketed by an additional G:G base pair either above or below. Those skilled in the art will appreciate that this condition is not sufficient to describe a G-quartet, although this condition is necessary. The final step in identification of a G-quartet is made visually on the screen as is identification of a stem structure, as will be discussed below with reference to specific examples.

$M_{ij}$ could also be input from other applications, most notably the energy matrix from a Zuker-Turner free energy evaluation. See Jaeger et al. (1989) Proc. Natl. Acad. Sci. USA 86:7706–7710 and Jaeger et al. (1990) Methods in Enzymology 183:281–306, the disclosures of which are incorporated by reference herein.

Following calculation of the base pair matrix at block 16, calculation of the covariation matrix at block 20 or calculation of the G-quartet matrix at block 22, at block 24 the matrix is drawn. At block 26 the controls are drawn and enabled and at block 28 the sequences are drawn with appropriate font, color and scrolling arrows. A sample screen including these elements displaying a base pair matrix calculated at block 16 is shown at FIG. 2. As seen in FIG. 2, the matrix calculated at block 16 is clearly symmetric about the diagonal $M_{ij}$. Likewise, a matrix calculated at block 20 or 22 would be symmetric about the diagonal $M_{ij}$.

In order to facilitate visual detection of conserved secondary structural elements, the preferred embodiment incorporates a color-coded representation of the "strength" of the consensus at each matrix position, the strength being the fraction of conserved secondary structural elements at a select point. Red indicates $M_{ij}=1.0$ (completely conserved secondary structural element defined by M), purple indicates $M_{ij}=0.75$ (75% conserved), dark-blue is $M_{ij}=0.5$ (50% conserved), light-blue indicates $M_{ij}=0.25$ (25% conserved) and white indicates $M_{ij}=0.0$ (complete absence of that secondary structure). For $M_{ij}$ between these values colors are generated in a continuum along the color spectrum. A strong consensus stem structure would be indicated as a contiguous red line perpendicular to the diagonal 102. For a given sequence set, a consensus matrix pattern is a signature of the consensus secondary structure. Quigley et al., supra, have provided a fairly complete description of the types of secondary structures represented by various matrix patterns.

The display illustrated at FIG. 2 shows the matrix 100 divided by this diagonal 102 into an upper portion 104 and a lower portion 106. The upper portion 104 and lower portion 106 are used for different display purposes. The upper portion 104 contains all the unfiltered data computed from the current alignment. The lower portion 106 is used to display filtered data. This will be discussed further below. To the left of the matrix 100 is a visual display of a portion of the aligned primary sequences 108. The controls drawn at block 26 are shown at 114. The controls provide for display of base pair, covariation or G-quartet matrices by making a desired selection at 116. The remaining controls of the control panel 114 are introduced and best understood with reference to the flow chart as it continues in FIG. 1B.

At decision block 30 it is determined whether the minimum base pair control has been changed. Minimum base pair control is element 118 in FIG. 2. The minimum base pair control 118 actuates a filter which selects a minimum stem length value between 1 and 6 which serves as the lower limit for the number of contiguous base pairs that make up a stem. For example, in FIG. 2 the minimum base pair selected is two so the lower portion 106 matrix shows stems having a length of 2 or greater. Returning to FIG. 1B, if at block 30 the minimum base pair threshold is changed by the user manipulating the control 118, at block 32 the lower portion 106 of the matrix is redrawn in accordance with the selection.

At decision block 34, following either no change in the minimum base pair or following redrawing of the lower portion 106 of the matrix, it is determined whether the display filter matrix has changed. The display filter control 120 is shown at FIG. 2. The display filter control 120 sets a threshold value on $M_{ij}$ for display. Only those $M_{ij}$ points with values above the threshold value will be displayed in the lower portion 106 of the matrix. In the case of the base pair matrix, the threshold value reflects the fraction of sequences in the multiple alignment which form a base pair at position i and j. In the case of the covariation matrix, the threshold value reflects the extent of base pair covariation for the individual sites. In the case of the G-quartet matrix, the threshold value reflects a fraction of sequences in the multiple alignment which potentially form quadruplex G:G base pairs consecutively with a stack height of at least 2. As should be readily apparent, the minimum base pairs and display filters require that any point which appears in the filtered lower matrix portion 106 satisfy both of the filter criteria. However, the two filters can be adjusted separately so that the consensus strength and stem length can be examined independently. If at decision block 34 the filter matrix is changed, at block 36 the lower portion 106 of the matrix is redrawn in accordance with the selected filter strength.

If at decision block 34 the display filter matrix is not changed or following redrawing of the lower portion 106 of the matrix at block 36, at decision block 38 it is determined whether the conserved base threshold has been changed. Referring to FIG. 2, the conserved base threshold control is element 122. This filter controls the threshold level for displaying nucleotide base conservation. The primary purpose of this filter is to allow for monitoring a primary sequence alignment while optimizing the consensus secondary structure during sequence alignment. Following election of a level of conserved base threshold, the sequence display 108 is redrawn at 40.

Following determination whether the conserved base threshold has changed at decision block 38 or following redrawing of the sequence display at block 40, at decision block 42 it is determined whether the sweep effect has been changed. The sweep effect control is illustrated at 124 of FIG. 2. The sweep effect control 124 allows for selection of the sweep effect for one base pair, including any base pair of a stem, or a stem such as the stem 107 of FIG. 2. A detailed description of the sweep effect will be provided with reference to blocks 58 and 60 of FIG. 1C. If the sweep effect is changed at decision block 42, at block 44 an appropriate variable of "stem" or "one" is set for future sweeps.

Because of limitations in the size of the display 100, in some cases not all of the multiple sequence alignment can be viewed at once. The program thus includes a scrolling option to display various portions of sequence sets. The scrolling includes a vertical scroll control 128 and a horizontal scroll control 130 as seen in FIG. 2. At decision block 46 the routine determines whether the horizontal scroll bar 130 has been moved. Scrolling horizontally allows a different set of twelve sequences to be visible. It is important to note, however, that sequences not displayed are still included in the structure matrix computation. If the horizontal scroll bar is moved at decision block 46, at block 48, the sequence display 108 is redrawn to reflect the currently elected portion of the sequence set at block 48. At decision block 50 it is determined whether the vertical scroll bar has been moved. The vertical scroll moves along the length of the aligned sequences. The 5' end of the sequences is at the top of the screen. If the 3' end extends farther than 50 positions beyond the 5' end, the present embodiment of the invention requires scrolling down to view it. Because of the limitation imposed on the present embodiment by the size of the smallest legible screen font, no base pair separated by an i–j length greater than 50 can be seen in the matrix for individual base pair resolution. If at decision block 50 it is determined that the vertical scroll bar has been moved, at block 52 the scrolling is illustrated by a re-display of both the upper and lower portions 104, 106 of the matrix and the displayed portion 108 of the primary sequences. It is important to note that the limitation of 50 nucleotides is not considered a significant problem since secondary structures tend to form locally and relevant regions of interest are usually less than 30 nucleotides long. Screens with a higher resolution than 640 ×480 (standard VGA) automatically expand the field of display accordingly.

Figure 23:
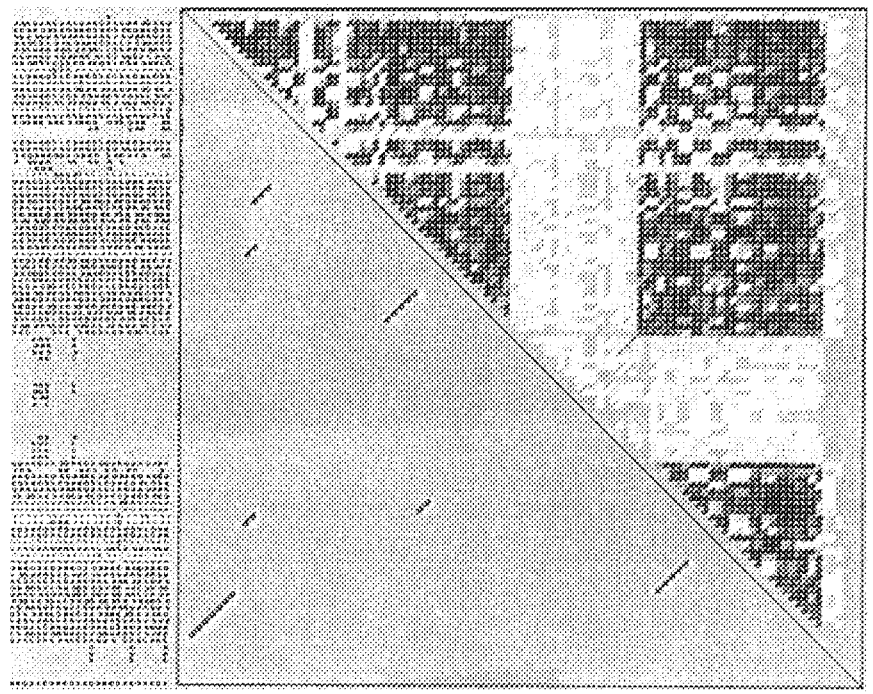
FIGS. 23 and 24 depict computed consensus base pair matrixes for a set of 40 transfer RNA sequences known to have "clover leaf" secondary structure.
Figure 24:
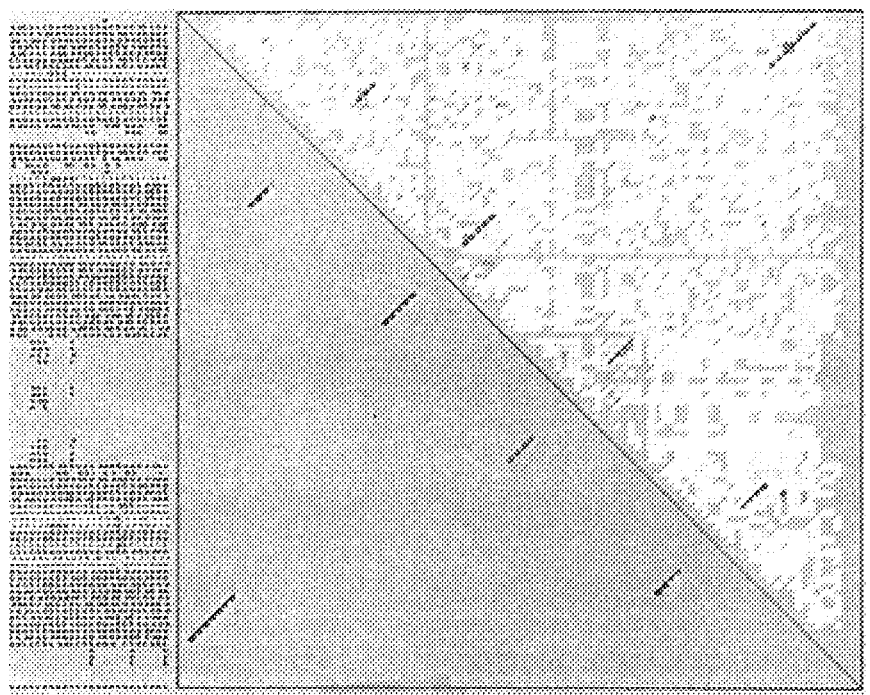

At decision block 54 it is determined whether a zoom feature has been enabled. This control is element 134 of FIG. 2. If the zoom button is enabled, at block 56 the entire matrix is redrawn and displayed at a reduced resolution. Examples of such screens are seen in FIGS. 23 and 24.

Figure 3:
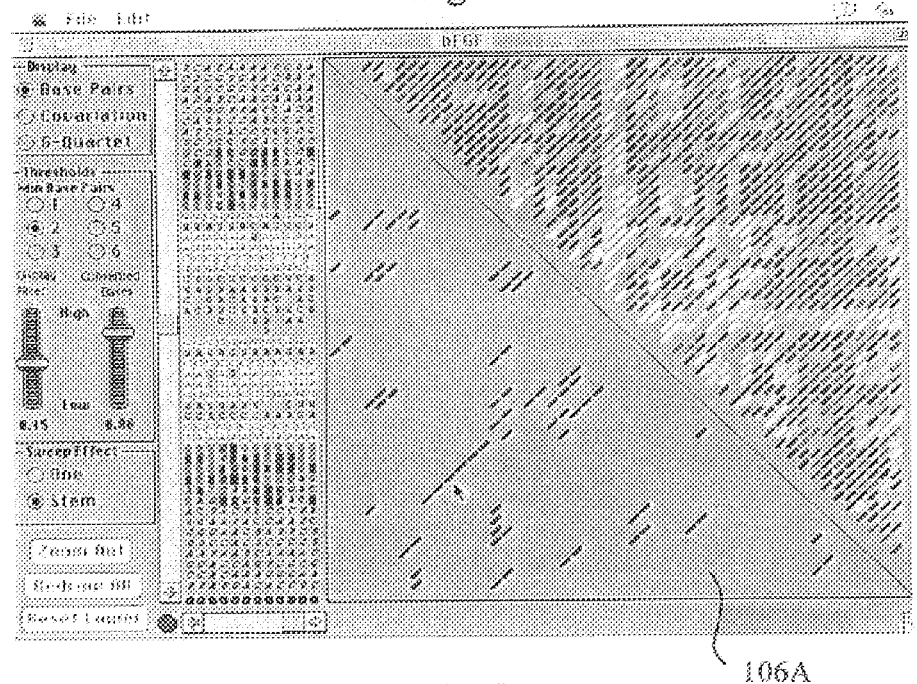
Figure 5:
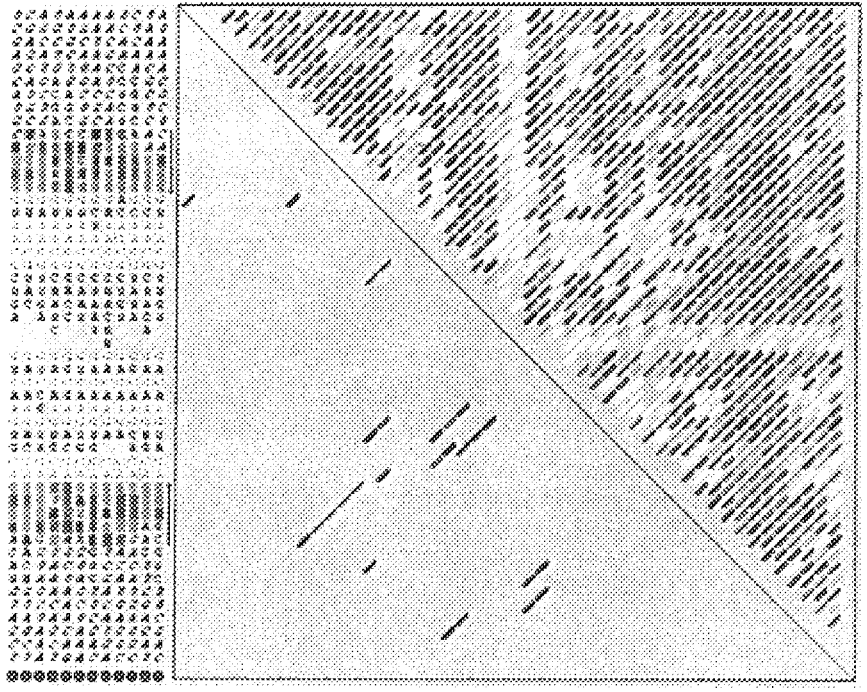
FIG. 5 is a base pair matrix of the alignment of the sequences of FIG. 4.
Figure 6:
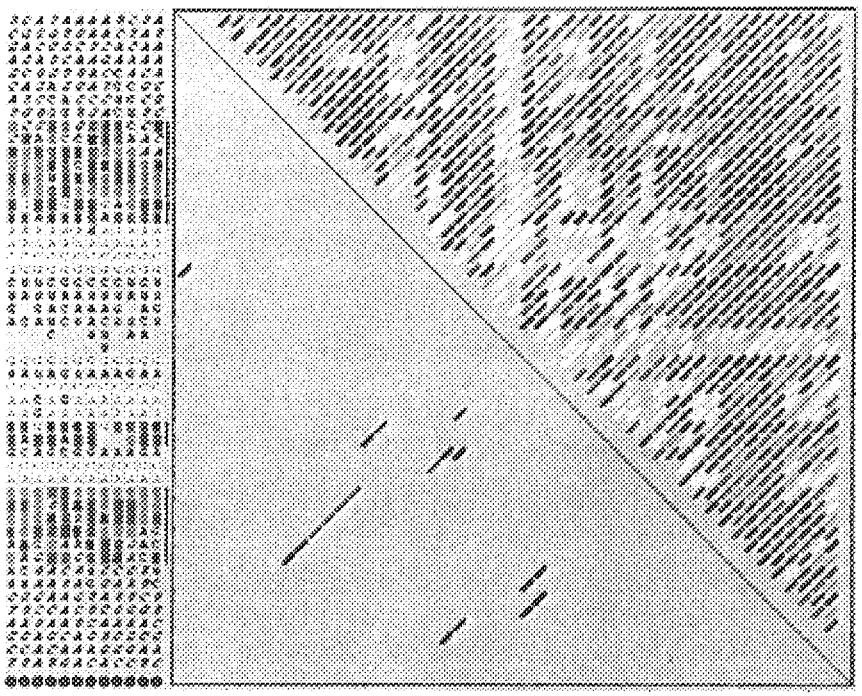
FIG. 6 is a base pair matrix of a revised alignment of the sequences of FIG. 4.
Figure 7:
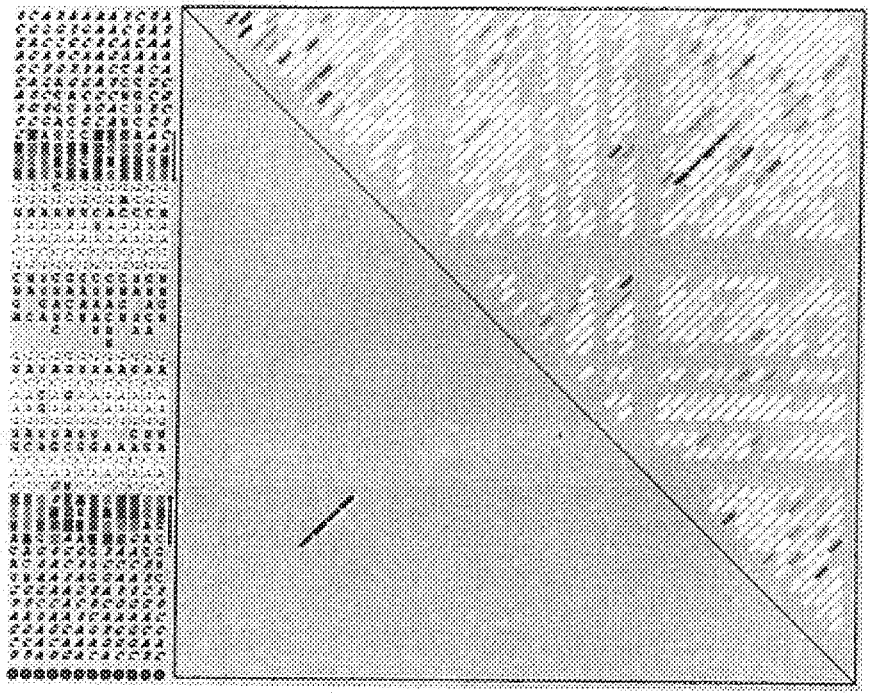
FIG. 7 is a display of a covariation matrix of the sequence alignment shown in FIG. 6.

At decision block 58 it is determined whether a base pair or base pairs comprising a stem has been selected in the lower triangle for sweep effect. Following setting of the filters as discussed above, the display of the lower portion 106 of the matrix typically exhibits numerous alternative structures. Any part of one stem that lies within either the range of rows or the range of columns of another stem can not simultaneously exist, since this would indicate that a nucleotide simultaneously forms a base pair with more than one residue. This is illustrated in FIG. 2. The range of rows and columns for the stem 107 are illustrated by the vertical 140 and horizontal lines 142 of FIG. 2. As described above, the structures within these vertical 140 and horizontal 142 lines can not coexist with the stem 107. As an aide to elucidating a consensus secondary structure, the program allows a user to interactively select a stem with concomitant elimination of all competing base pairs. As shown in FIG. 2, arrows 144 are drawn in the sequence alignment display over the nucleotides forming the stem. Each base pair within the selected stem is highlighted with one of the six color coded backgrounds, one for each of the expanded Watson-Crick base pairs. This serves as a visual cue for identifying base pair and base pair covariation at select positions. With the sweep effect control 124 on stem as indicated in FIG. 2, the competing base pairs are "swept out" in accordance with the sweep effect selected at block 42 and the lower portion 106 of the matrix is redrawn at block 60 and the resulting redrawn portion 106 of the matrix 106A is illustrated in FIG. 3.

At decision block 62 it is determined whether a user has adjusted sequence alignment. The present invention provides for realignment of an original alignment of a set of related sequences. This is significant because the original alignment is generally done without consideration of secondary structure. The present invention allows for repositioning of one sequence relative to the remaining set, for gap placement within a sequence, or for removal of a sequence set. Realignment is achieved by a user placing a cursor over a select nucleotide of a nucleotide sequence and dragging the cursor either up or down to introduce or close a gap. In addition, the cursor can be moved to the top of a sequence to reposition the sequence relative to the entire sequence set. Should the user make such an adjustment, at block 64 the primary sequences are realigned in accordance with the user's directions and the matrix is redrawn. In this manner, a user can determine quickly whether repositioning enhances the secondary consensus structure or not so alternative repositioning can be investigated. At decision block 66 it is determined whether the program should quit. If yes, the program ends. If not, it is continued at C in FIG. 1A.

Figure 25:
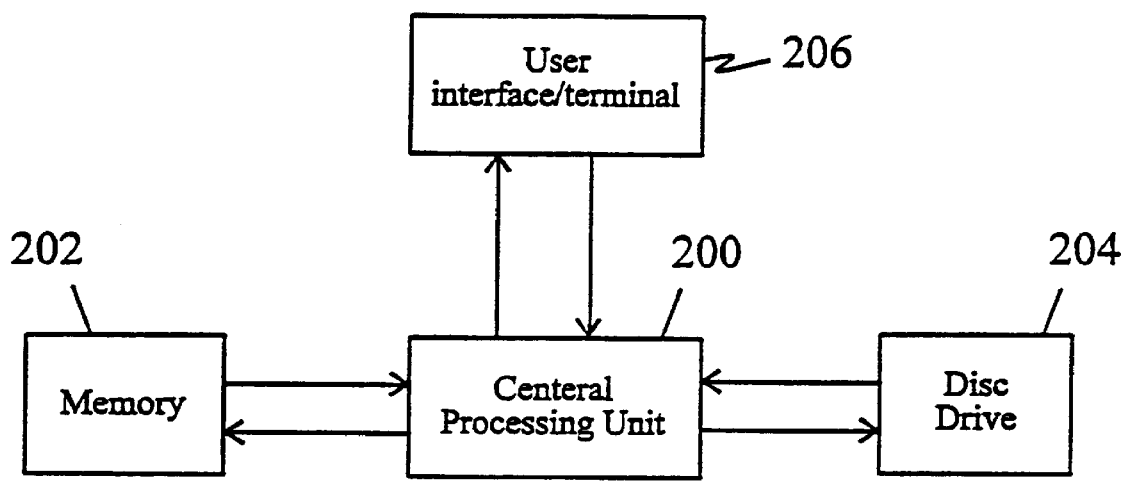
FIG. 25 is a schematic representation of computer hardware for use in the present invention.

FIG. 25 is a schematic representation of a computer hardware system for running the computer program described above. The hardware incudes a central processing unit 200, an associated memory 202, a disc drive 204 and a user interface/terminal 206. The user interface/terminal 206 displays the screens in FIGS. 2–3 described above and FIGS. 4–24 described below. The configuration is conventional as readily understood by one skilled in the art.

The utility of the present invention is best understood with reference to several examples.

EXAMPLE 1

Figures 8, 9, 10:
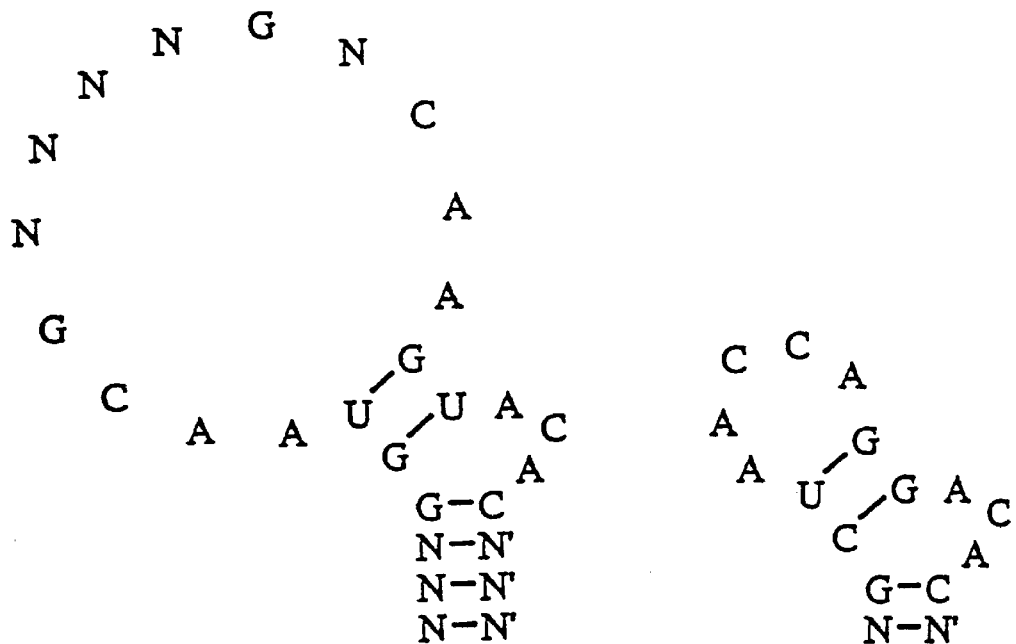
FIG. 8 (SEQ ID NO: 23) is a schematic display of the secondary consensus structure translated from FIGS. 6 and 7.
FIG. 9 (SEQ ID NO: 24) illustrates the consensus structural motif for a related family of molecules.
FIG. 10 (SEQ ID NO: 25–SEQ ID NO: 28) is the primary sequence of RNA molecules known to bind to the broncodilator theophylline.

As a first example we consider a group of RNA sequences that were selected for high-affinity binding to basic fibroblast growth factor (bFGF). Two distinct ligand families have been identified based on sequence and secondary structure similarities. See Jellinek et al. (1993) Proc. Natl. Acad. Sci. USA 90:11227–11231, which is incorporated by reference herein. Family 1 ligands are characterized by a consensus secondary structure motif that has a variable length stem with a three nucleotide bulge followed by a highly conserved five nucleotide loop. Most family 1 ligands bind to bFGF with dissociation constants of 3–20 nM. Family 2 is the larger of the two sequence sets (22 sequences, see FIG. 4) and contains the highest affinity ligands, some of which bind to bFGF with dissociation constants as low as 0.2 nM. A common secondary structure motif for family 2 sequences has been identified by inspection and consists of a variable length stem closing a 19–22 nucleotide loop that contains significant sequence conservation. The structure matrix for the published alignment of these sequences is presented in FIG. 5. The data has been filtered with a two base pair minimum for stem formation, and a threshold of 0.51 and 0.80 for consensus structure and conserved residues, respectively. The alignment at the left shows several distinct regions of highly conserved bases, highlighted in white. The stem is easily identified as the long run of 5 contiguous base pairs which show strong consensus and covariation. Several possible structures are evident within the loop region. The short stem of 2 nucleotides, which results in the formation of a bulge within the main stem, allows this family of molecules to adopt a structural motif more similar to family 1. The revised alignment, in which this motif is enhanced, is presented in FIGS. 6–7 with both a base pair and covariation display. The former shows an extension of the primary stem by one base pair and the latter indicates significant covariation is present in this stem. The resulting secondary consensus structure is translated and schematically displayed in FIG. 8. FIG. 9 illustrates for comparison the consensus structural motif of family 1 molecules. The sequence conservation in the bulge and loop regions for the two motifs is worth noting. Clearly, these two sets of sequences appear to share a structural motif which was recognized only after an examination of the consensus structure matrix presented here.

EXAMPLE 2

Figure 11:
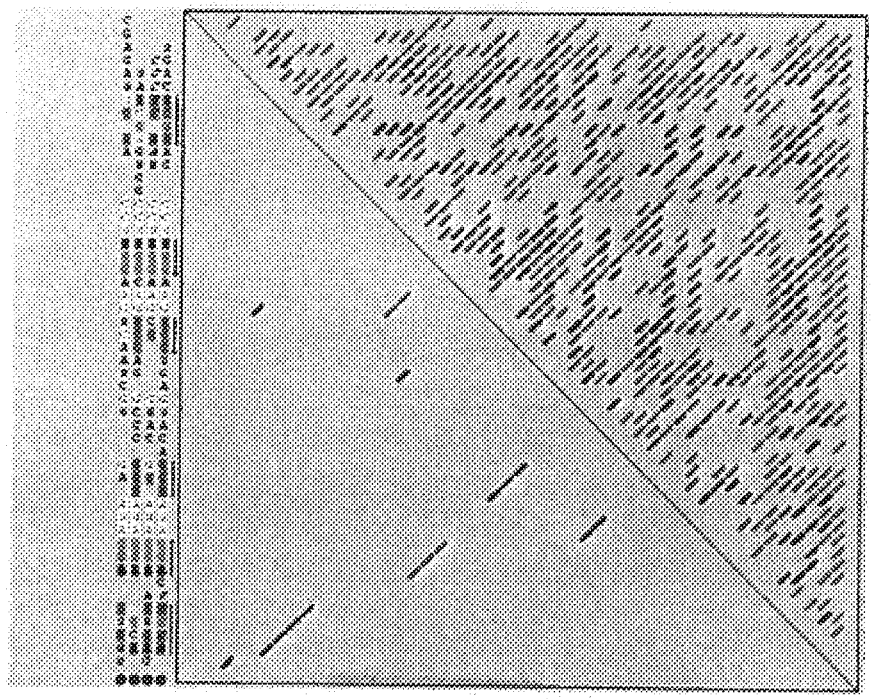
FIG. 11 shows the base pair matrix resulting from the initial alignment of the sequences in FIG. 10.
Figure 12:
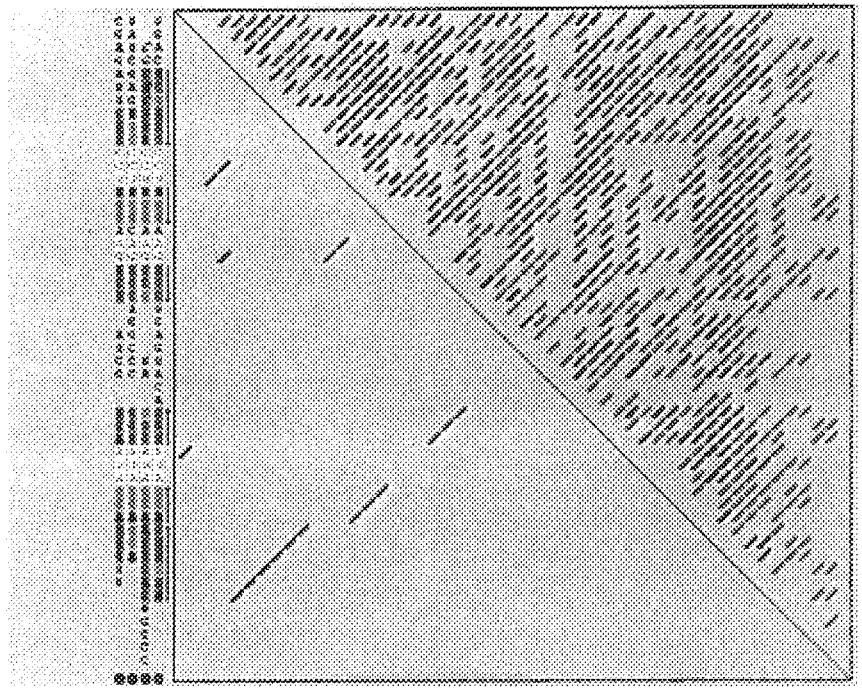
FIGS. 12 and 13 illustrate consensus structures resulting from realignment of the sequence sets of FIG. 10.
Figure 13:
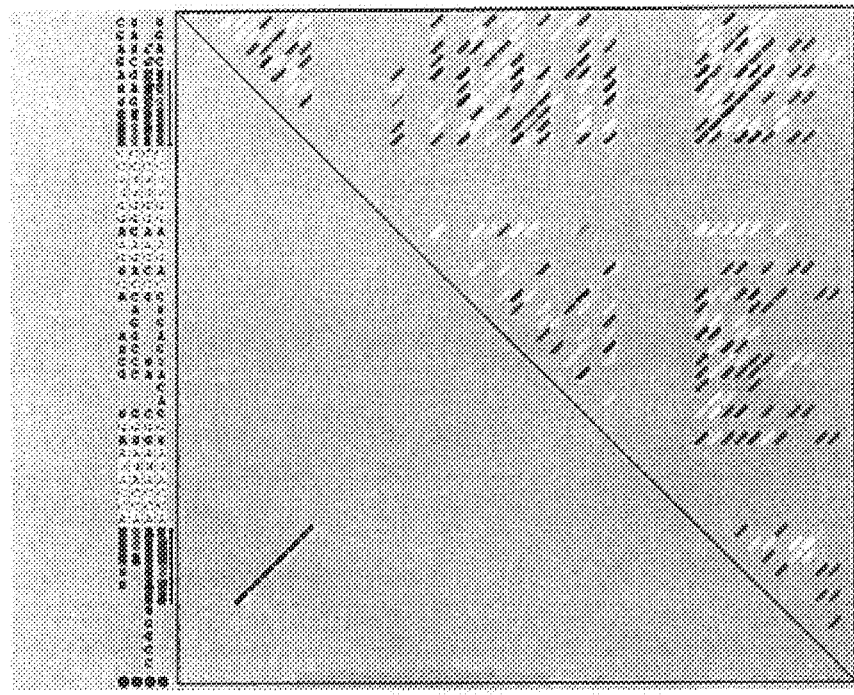
Figures 14, 15:
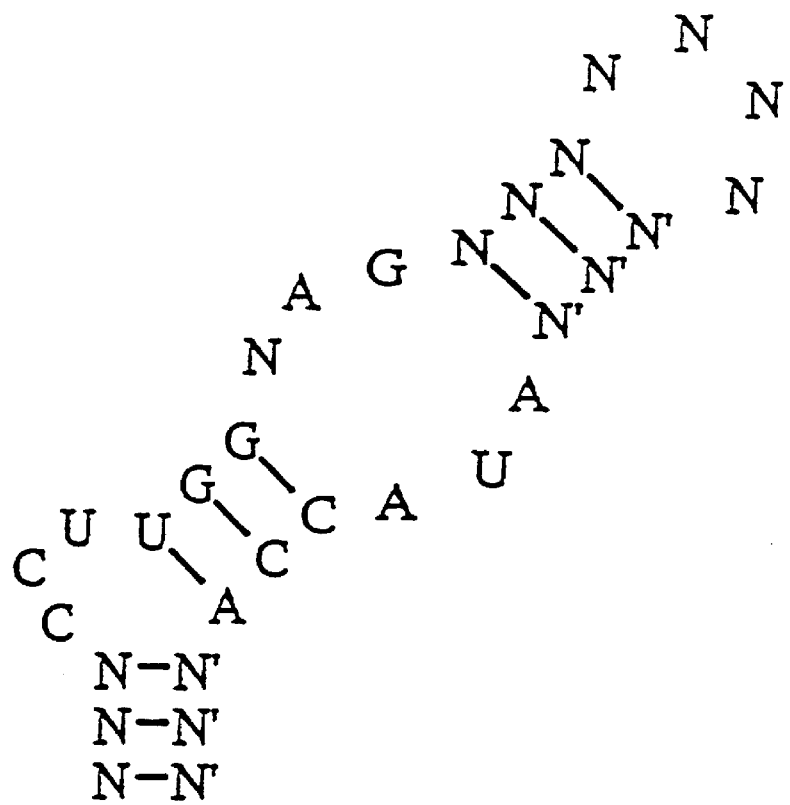
FIG. 14 (SEQ ID NO: 29) is a schematic of the secondary consensus structure of the matrixes of FIGS. 12 and 13.
FIG. 15 (SEQ ID NO: 30–SEQ ID NO: 37) is a group of sequence-related RNA molecules that bind to HIV-1 reverse transcriptase.

The next example we consider is a set of RNA molecules that were selected for their ability to bind the bronchodilator theophylline with high affinity (low micromolar range) and in enormous preference over caffeine (>10,000-fold lower affinity), a compound which differs from theophylline by a single methyl group at the N-7 position. See Jenison et al. (1994) Science 263:1425–1428, which is incorporated by reference herein. FIG. 10 displays the sequence set and FIG. 11 shows the structure matrix resulting from the initial alignment, displayed to the left. In this case the lower left triangle has been filtered with a three base pair minimum for stem formation, a threshold of 0.45 and 0.80 for consensus structure and conserved residues, respectively. The alignment algorithm finds two distinct regions of highly conserved bases, highlighted in white. The most conserved secondary structure is a short stem of length three formed by six absolutely conserved residues. Hence, no base pair covariation is observed in this stem. Two other less conserved stems encompassing more variable positions also appear in the lower left triangle. With this as the starting point, we were able to optimize the degree of consensus structure formation by refining the original alignment, as illustrated in FIGS. 12 and 13. Strong consensus structures for all three stems are now observed. The two outermost structures are seen to covary significantly (see FIG. 13). This covariation is a strong indication of structure and is not obvious in the original sequence alignment (FIG. 11). The resulting secondary structure motif for this set of molecules embodied in the matrix is shown in FIG. 14.

EXAMPLE 3

Figure 16:
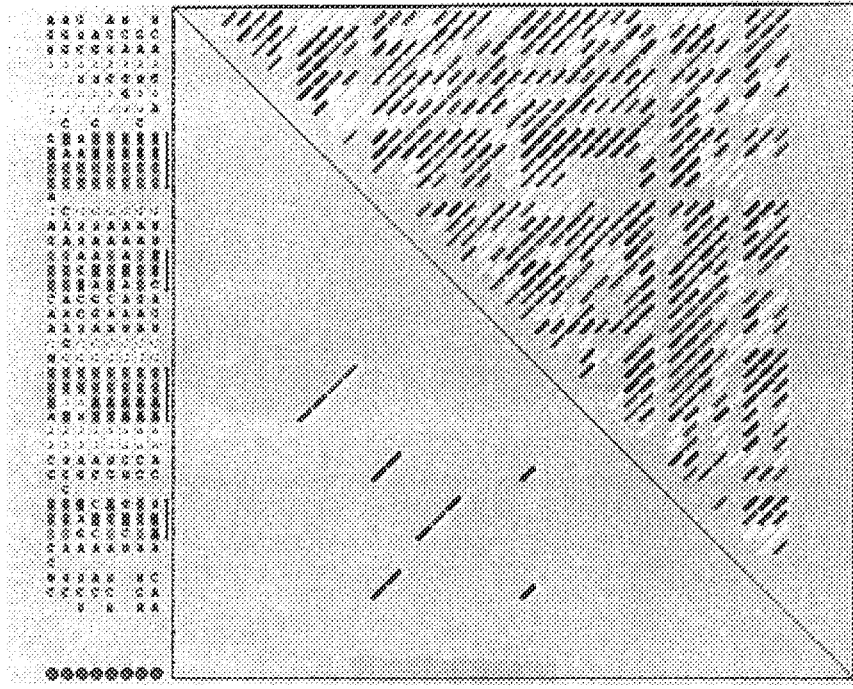
FIG. 16 is the initial base pair matrix derived from the sequence shown in FIG. 15.
Figure 17:
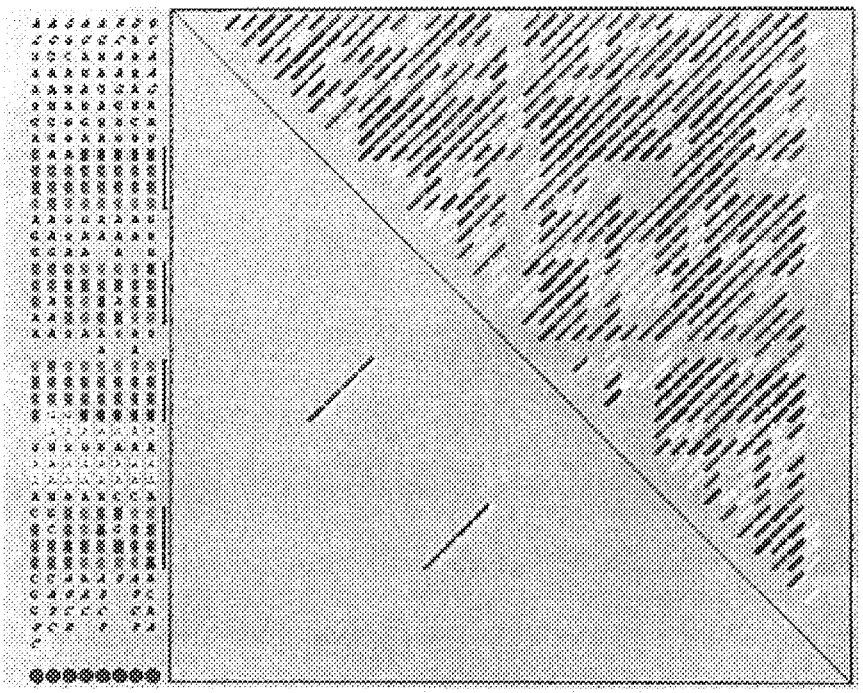
FIG. 17 illustrate the resulting base pair matrix following realignment of the sequence of FIG. 15.
Figure 18:
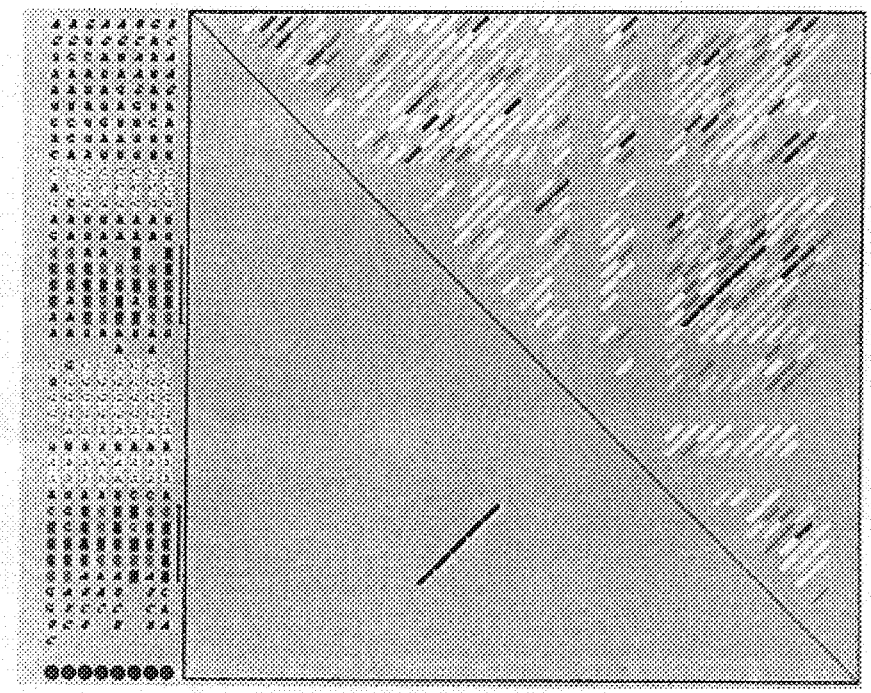
FIG. 18 is the covariation matrix of the realignment shown in FIG. 17.
Figure 21:
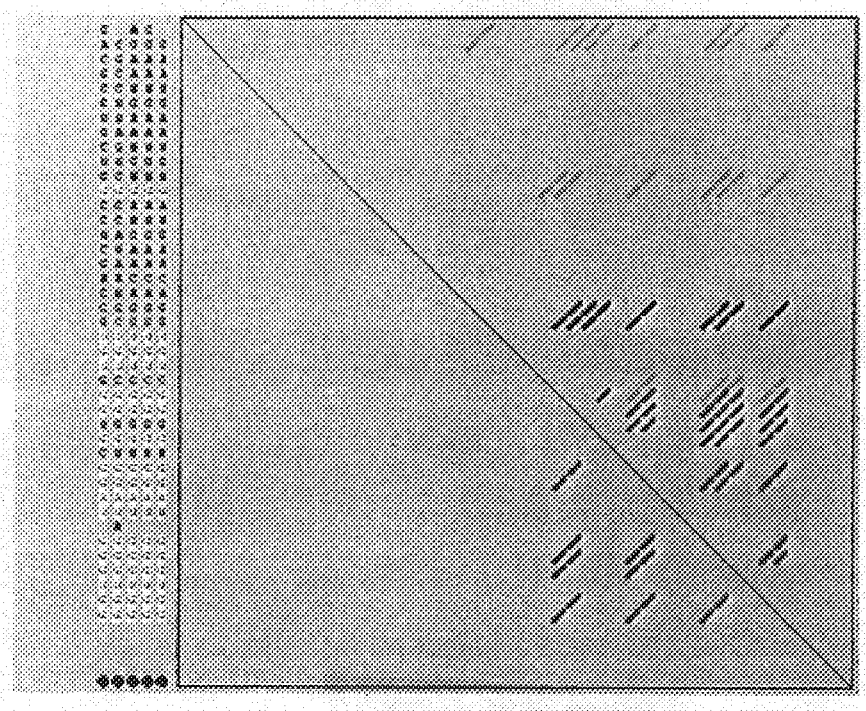
FIG. 21 is the resulting G-quartet base pair matrix of the sequences in FIG. 20.
Figures 19, 20:
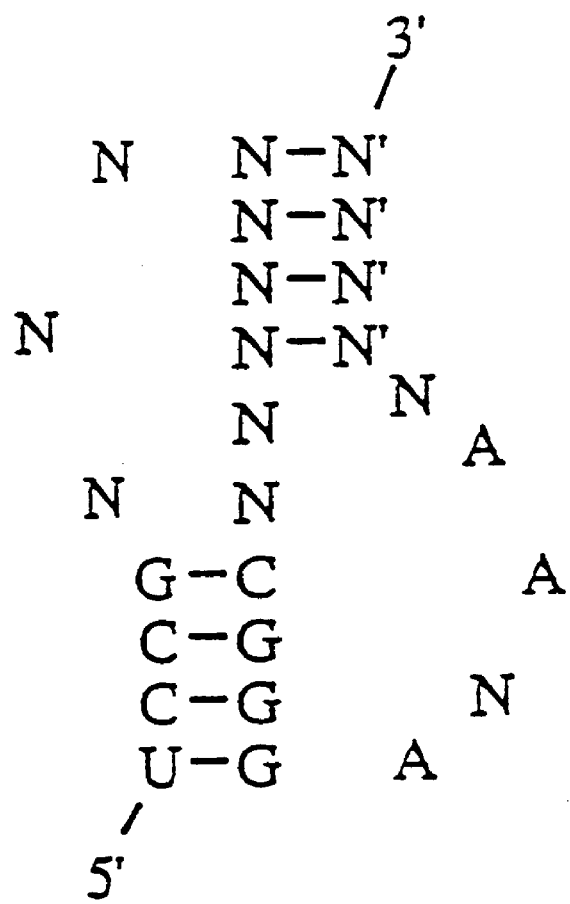
FIG. 19 (SEQ ID NO: 38) is the schematic secondary consensus structure depicted in FIGS. 17 and 18.
FIG. 20 (SEQ ID NO: 39–SEQ ID NO: 43) is a set of sequences containing modified ribose moieties for pyrimidine bases.

The next example is a group of sequence-related RNA molecules that bind to HIV-1 Reverse Transcriptase with high affinity, see Tuerk et al. (1992) Proc. Natl. Acad. Sci. USA 89:6988–6992, which is incorporated by reference herein, illustrated in FIG. 15. The structure matrix derived from the initial multiple sequence alignment is shown in FIG. 16 with a two base pair minimum for stem formation and a threshold of 0.05 and 0.80 for consensus structure and conserved residues, respectively. To the left of the matrix, two regions of conserved primary structure are highlighted in white. The strongest consensus structure, a four base pair stem, is formed between the two conserved sequence regions. Three other possible structures are apparent, only one of which has a stem length of three. Examination of the alignment surrounding these structures allows for a new alignment to be proposed which dramatically enhances the three base pair stem as well as the four base pair stem formed in the conserved sequence regions. The resulting structure matrix is displayed in FIGS. 17–18 and the secondary structure is schematically presented in FIG. 19. Two variable length stems, from three to five base pairs each, are seen to result in a pattern indicative of a pseudo-knot. All of the conserved residues are found in the upper stem, while the lower stem has a variable composition with extensive base paring covariation. This is clearly illustrated in FIG. 18, where the structure is viewed as a covariation matrix. Since base pair covariation occurs much less frequently than base pairing, the covariation structure matrix is less crowded. With lower background, positions where base pair covariation is significant are readily detected even without filtering as evidenced in the upper right triangle of FIG. 18.

EXAMPLE 4

Figure 22:
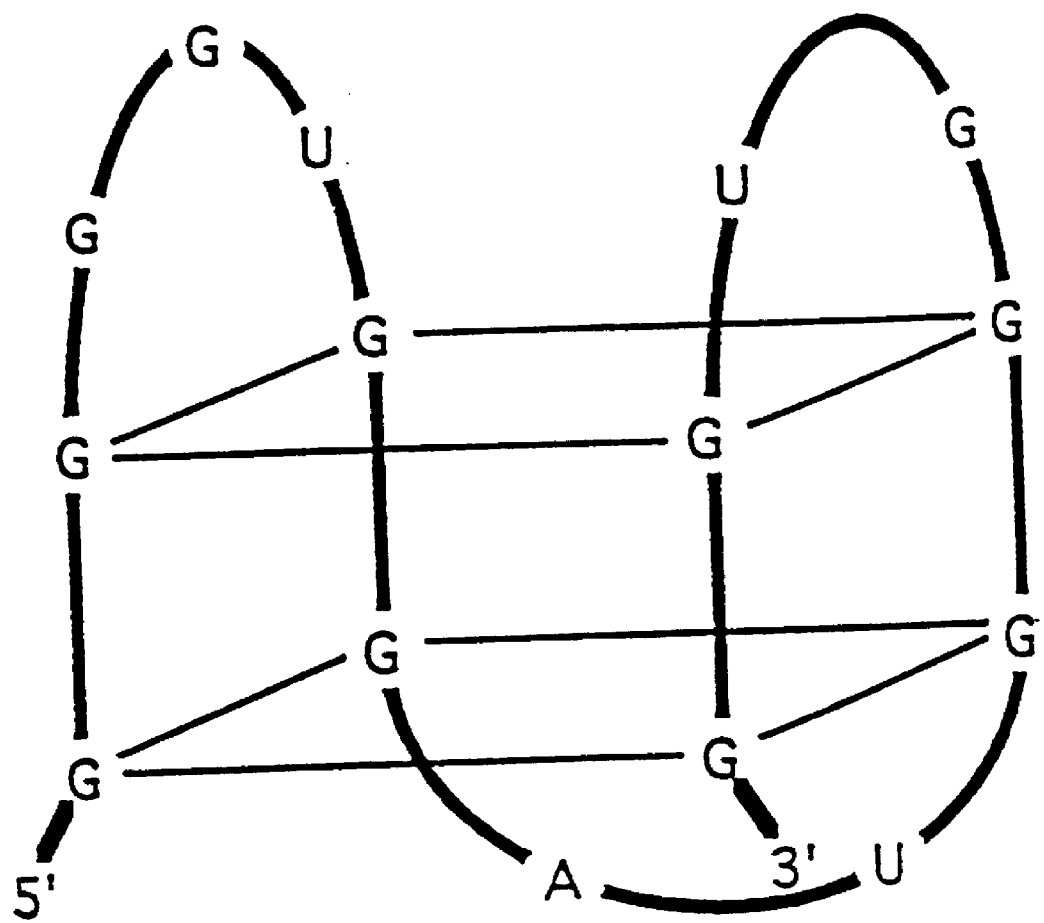
FIG. 22 (SEQ ID NO: 44) is a schematic of the secondary consensus structure translated from FIG. 21.

As the next example, we present the consensus structure results for a set of sequences containing modified ribose moieties for pyrimidine bases, namely a 2'-amino substituted for the 2'-hydroxy of RNA. The SELEX procedure was used to isolate 2'-amino-RNA molecules, FIG. 20, which bind to human neutrophil elastase. These molecules are quite G-rich and were determined to be consistent with folding into a G-quartet motif. The resulting G-quartet structure matrix is displayed in FIG. 21. There are many regions of conserved sequence, primarily G residues, that appear in the alignment. The characteristic pattern of the G-quartet formation, a set of at least two contiguous G's interacting with three other sets of contiguous G's, takes the form of a structure triangle in the lower left triangle of FIG. 21, comprised of six pairs of G—G bases. The resulting secondary structural motif for this set of molecules embodied in the matrix is shown in FIG. 22.

EXAMPLE 5

A final example illustrates the utility of the cumulative dot matrix method for application to molecular taxonomy. FIGS. 23 and 24 show computed consensus structure matrix for a set of 40 transfer RNA (tRNA) sequences, all of which have a well-know "cloverleaf" secondary structure. The 40 aligned sequences were selected at random from the EMBL tRNA database of over 2000 sequences. See Steinberg et al. (1993) Nucleic Acid Res. 21:3011–3015, which is incorporated by reference herein. FIG. 23 illustrates the base pair matrix and FIG. 24 illustrates the covariation matrix. The secondary structure comprising four stems is clearly illustrated by the four red diagonals of three to seven base pairs in length observed in FIG. 23. In addition to these secondary structure interactions, several known tertiary contacts are also found, namely, base pairs at positions 8/14, 18/55 and 19/56. These are not unique. Several other potential base pairs that do not correspond to any known tertiary contacts can be observed in FIG. 23. The covariation display is seen to highlight the four stems of tRNA dramatically and a new stem not seen in the base pair display is observed. This corresponds to the extra arm seen in some tRNAs in the so-called variable region. No tertiary contacts are seen in FIG. 24 in contrast to a similar analysis in Gutell et al. (1992) Nucleic Acid Res. 20:5785–5795. This is most likely due to the limited sampling size of 40 sequences.

The present invention provides an expedient solution to the problem of determining a conserved secondary structure motif of a set of functionally related oligonucleotide sequences. Beginning with a predetermined set of multiple sequences aligned using known techniques, secondary structure can be found through optimization of the initial alignment. The method allows for the simultaneous examination of all possible secondary structures resulting from an initial multiple sequence alignment. The present method therefore reduces the likelihood of overlooking a significant component of the consensus secondary structure. Although most of the examples set forth herein are derived from SELEX process experiments, this method can clearly be applied to many functionally related oligonucleotide sequences, such as phylogenetic data sets as illustrated in Example 5.

What is claimed is:

1. A method for identifying consensus secondary structures for a plurality of nucleic acid sequences having a select functional relatedness comprising the steps of:
   a) aligning the plurality of oligonucleotide sequences according to primary structure similarity;
   b) providing a computer system including a central processing unit, associated memory and a visual display;
   c) inputting into the associated memory the plurality of oligonucleotide sequences;
   d) computing using the central processing unit a matrix representing the strength of a select property determinant of secondary structure between nucleotides of each aligned oligonucleotide sequence;
   e) visually displaying the matrix representing the strength of the select property determinant of secondary structure, thereby displaying all possible secondary structures of the aligned sequences;
   f) identifying relatively high-strength consensus structure; and
   g) realigning the inputted plurality of oligonucleotide sequences of step a) and repeating steps d) and e) as necessary to enhance the strength of the identified consensus stem structures.

2. The method of claim 1 wherein in step d) the select property determinant of secondary structure is Watson-Crick base pairing.

3. A method for identifying consensus secondary structures for a plurality of nucleic acid sequences having a select functional relatedness comprising the steps of:
   a) aligning the plurality of oligonucleotide sequences according to primary structure similarity;
   b) providing a computer system including a central processing unit, associated memory and a visual display;
   c) inputting into the associated memory the plurality of oligonucleotide sequences;
   d) computing using the central processing unit a matrix using the following equation:

$$M_{ij}=1/N \; \Sigma_n\Sigma_{b:b'}C(b:b')\delta(a_{n,i}-b)\delta(a_{n,j}-b')$$

where $M_{ij}$ is the relative strength of base paring between nucleotides at a position i and a position j of the matrix, $a_{n,i}$ designates a nucleotide at a position i of a sequence n in an N-sequence multiple alignment, b:b' indicate one of the four Watson-Crick or two G:U base pairs, C(b:b') is a select general coefficient and $\delta(a_{n,i}-b)$ is the Kronecker delta function, which is equal to 1 if $a_{n,i}$=b, and is otherwise equal to 0;
   e) visually displaying the matrix, thereby displaying all possible secondary structures of the aligned sequences; and
   f) identifying relatively high-strength consensus structures.

4. The method of claim 3 further comprising:
   filtering from display in step e) elements of the matrix having a strength of less than a select amount.

5. The method of claim 3 further comprising filtering from display in step e) stem structures of a length less than a select number of nucleotide base pairs.

6. The method of claim 1 wherein in step d) the select property determinant of secondary structure is base pairing covariation.

7. The method of claim 1 further comprising:
   filtering from display in step e) elements of the matrix having a strength of less than a select amount.

8. The method of claim 1 wherein in step e) the relative strength of consensus base pairing is indicated by displaying a dot at each position $M_{ij}$ of the matrix in a color corresponding to its strength of consensus base pairing.

9. The method of claim 1 further comprising filtering from display in step e) stem structures of a length less than a select number of nucleotide base pairs.

10. A method for identifying consensus secondary structures for a plurality of nucleic acid sequences having a select functional relatedness comprising the steps of:
    a) aligning the plurality of oligonucleotide sequences according to primary structure similarity;
    b) providing a computer system including a central processing unit, associated memory and a visual display;
    c) inputting into the associated memory the plurality of oligonucleotide sequences;
    d) computing using the central processing unit a matrix computed using the following equation:

$$M_{ij}=\frac{1}{2}(\Sigma_{b:b'}f_{bi,b'j} \; \log_2[f_{bi,b'j}/f_{bi}f_{b'j}])$$

where $$f_{bi}=1/N\Sigma_n\delta(a_{n,i}-b),$$

$$f_{bi,b'j}=1/N\Sigma_n\delta(a_{n,i}-b) \; \delta(a_{n,j}-b'),$$

$f_{bi}$ is the fraction of sequences which have a base b at position i in the multiple alignment, and $f_{bi, b'j}$ is the fraction of sequences which form a b:b' base pair at positions i and j;
    e) visually displaying the matrix, thereby displaying all possible secondary structures of the aligned sequences; and
    f) identifying relatively high-strength consensus stem structures.

11. The method of claim 10 further comprising:
    filtering from display in step e) elements of the matrix having a strength of less than a select amount.

12. The method of claim 10 further comprising filtering from display in step e) stem structures of a length less than a select number of nucleotide base pairs.

13. A system for identifying consensus secondary structures for a plurality of nucleic acid sequences having a select functional relatedness comprising:
    input means for inputting into an associated memory a plurality of functionally related oligonucleotide sequences aligned according to primary structure similarity;
    a central processing unit coupled to the associated memory;
    a display coupled to the central processing unit;
    the central processing unit being preprogrammed to compute from the inputted oligonucleotide sequences a matrix representing the strength of a select property determinant of consensus stem structure between nucleotides of each aligned oligonucleotide sequence;
    the central processing unit further being programmed to identify consensus structures of a select strength from the computed matrix;
    the central processing unit outputting to the display the consensus structures of the select strength and all possible secondary structures of the aligned sequences.

14. The system of claim 13 wherein the central processing unit is preprogrammed for varying the select strength.

15. The computer system of claim 13 wherein the central processing unit is further preprogrammed for identifying consensus stem structures of a length greater than or equal to a select number of nucleotide base pairs.

16. A computer-readable storage medium containing computer readable instructions that when executed by a computer connected to a display, performs the steps comprising:

retrieving from a memory coupled to the computer a data set comprising a select plurality of aligned functionally related oligonucleotide sequences;

selectively calculating one of a Watson-Crick base pair matrix, a covariation matrix and a G-Quartet matrix; and outputting on the display the calculated matrix, the matrix showing all possible secondary structures of the aligned sequences.

17. The computer-readable storage medium of claim 16 further performing the step comprising:

outputting on the display a plurality of controls for varying the output of the calculated matrix.

18. The computer-readable storage medium of claim 16 further performing the step comprising:

filtering from a portion of the outputted matrix base pairing of less than a select strength.

19. The computer-readable storage medium of claim 16 further performing the step comprising:

filtering from a portion of the outputted matrix consensus stem structures less than a select length.

20. The computer-readable storage medium of claim 16 further performing the step comprising:

sweeping from a portion of the display any base pair conflicting with a select base pair.

* * * * *

SEQUENCE LISTING ( 1 ) GENERAL INFORMATION:

( i i i ) NUMBER OF SEQUENCES: 44

( 2 ) INFORMATION FOR SEQ ID NO:1:

( i ) SEQUENCE CHARACTERISTICS:
        ( A ) LENGTH: 77 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GGGAGCUCAG   AAUAAACGCU   CAAGGGUAAC   GUUGUGACAA   GUACACCUGC            50

GUCUUCGACA   UGAGGCCCGG   AUCCGGC                                        77
```

( 2 ) INFORMATION FOR SEQ ID NO:2:

( i ) SEQUENCE CHARACTERISTICS:
        ( A ) LENGTH: 77 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
GGGAGCUCAG   AAUAAACGCU   CAAGGGGCAA   CGCUACAGAC   AAGUGCACCC            50

AACUUCGACA   UGAGGCCCGG   AUCCGGC                                        77
```

( 2 ) INFORMATION FOR SEQ ID NO:3:

( i ) SEQUENCE CHARACTERISTICS:
        ( A ) LENGTH: 77 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
GGGAGCUCAG   AAUAAACGCU   CAACGUCAGA   AGGCAACGUA   UAGGCAAGCA            50

CACUUCGACA   UGAGGCCCGG   AUCCGGC                                        77
```

( 2 ) INFORMATION FOR SEQ ID NO:4:

( i ) SEQUENCE CHARACTERISTICS:
        ( A ) LENGTH: 77 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
GGGAGCUCAG   AAUAAACGCU   CAACCUCUCG   AAGACAACGC   UGUGACAAGA            50

CACUUCGACA   UGAGGCCCGG   AUCCGGC                                        77
```

( 2 ) INFORMATION FOR SEQ ID NO:5:

( i ) SEQUENCE CHARACTERISTICS:
        ( A ) LENGTH: 77 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
GGGAGCUCAG  AAUAAACGCU  CAAAGUGGGA  AACGCUACUU  GACAAGACAC        50
CACUUCGACA  UGAGGCCCGG  AUCCGGC                                   77
```

( 2 ) INFORMATION FOR SEQ ID NO:6:

( i ) SEQUENCE CHARACTERISTICS:
        ( A ) LENGTH: 77 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
GGGAGCUCAG  AAUAAACGCU  CAAGGCUACG  CUAAUGACAA  GUGCACUUGG        50
GUGUUCGACA  UGAGGCCCGG  AUCCGGC                                   77
```

( 2 ) INFORMATION FOR SEQ ID NO:7:

( i ) SEQUENCE CHARACTERISTICS:
        ( A ) LENGTH: 79 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
GGGAGAUGCC  UGUCGAGCAU  GCUGCUCUGG  UAACGCAAUG  UCAAGUGCAC        50
AUGAGUAGCU  AAACAGCUUU  GUCGACGGG                                 79
```

( 2 ) INFORMATION FOR SEQ ID NO:8:

( i ) SEQUENCE CHARACTERISTICS:
        ( A ) LENGTH: 79 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
GGGAGAUGCC  UGUCGAGCAU  GCUGAGCCGC  AGGUAACGGA  CCGGCGAGAC        50
CAUUGUAGCU  AAACAGCUUU  GUCGACGGG                                 79
```

( 2 ) INFORMATION FOR SEQ ID NO:9:

( i ) SEQUENCE CHARACTERISTICS:
        ( A ) LENGTH: 79 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
GGGAGAUGCC  UGUCGAGCAU  GCUGACGAGC  UUCGUAACGC  UAUCGACAAG        50
UGCAGUAGCU  AAACAGCUUU  GUCGACGGG                                 79
```

( 2 ) INFORMATION FOR SEQ ID NO:10:

( i ) SEQUENCE CHARACTERISTICS:
        ( A ) LENGTH: 79 BASE PAIRS (B) TYPE: nucleic acid
(C) STRANDEDNESS: single
(D) TOPOLOGY: linear (xi) SEQUENCE DESCRIPTION: SEQ ID NO:10:

GGGAGAUGCC UGUCGAGCAU GCUGAAGGGG AAACGUUGAG UCCGGUACAC          50

CCUGGUAGCU AAACAGCUUU GUCGACGGG                                79

(2) INFORMATION FOR SEQ ID NO:11:

(i) SEQUENCE CHARACTERISTICS:
(A) LENGTH: 79 BASE PAIRS
(B) TYPE: nucleic acid
(C) STRANDEDNESS: single
(D) TOPOLOGY: linear (xi) SEQUENCE DESCRIPTION: SEQ ID NO:11:

GGGAGAUGCC UGUCGAGCAU GCUGGAGGUA ACGUACGACA AGACCACUCC          50

AACUGUAGCU AAACAGCUUU GUCGACGGG                                79

(2) INFORMATION FOR SEQ ID NO:12:

(i) SEQUENCE CHARACTERISTICS:
(A) LENGTH: 79 BASE PAIRS
(B) TYPE: nucleic acid
(C) STRANDEDNESS: single
(D) TOPOLOGY: linear (xi) SEQUENCE DESCRIPTION: SEQ ID NO:12:

GGGAGAUGCC UGUCGAGCAU GCUGAGGUAA CGCUGAGUCA AGUGCACUCG          50

ACAUGUAGCU AAACAGCUUU GUCGACGGG                                79

(2) INFORMATION FOR SEQ ID NO:13:

(i) SEQUENCE CHARACTERISTICS:
(A) LENGTH: 79 BASE PAIRS
(B) TYPE: nucleic acid
(C) STRANDEDNESS: single
(D) TOPOLOGY: linear (xi) SEQUENCE DESCRIPTION: SEQ ID NO:13:

GGGAGAUGCC UGUCGAGCAU GCUGGGGAAA CGCUAUCGAC GAGUGCACCC          50

GGCAGUAGCU AAACAGCUUU GUCGACGGG                                79

(2) INFORMATION FOR SEQ ID NO:14:

(i) SEQUENCE CHARACTERISTICS:
(A) LENGTH: 79 BASE PAIRS
(B) TYPE: nucleic acid
(C) STRANDEDNESS: single
(D) TOPOLOGY: linear (xi) SEQUENCE DESCRIPTION: SEQ ID NO:14:

GGGAGAUGCC UGUCGAGCAU GCUGCCGAGG GUAACGUUGG GUCAAGCACA          50

CCUCGUAGCU AAACAGCUUU GUCGACGGG                                79

(2) INFORMATION FOR SEQ ID NO:15:

(i) SEQUENCE CHARACTERISTICS:
(A) LENGTH: 79 BASE PAIRS
(B) TYPE: nucleic acid
(C) STRANDEDNESS: single
(D) TOPOLOGY: linear (xi) SEQUENCE DESCRIPTION: SEQ ID NO:15:

```
GGGAGAUGCC UGUCGAGCAU GCUGUCGGGG UAACGUAUUG GCAAGGCACC            50

CGACGUAGCU AAACAGCUUU GUCGACGGG                                    79
```

( 2 ) INFORMATION FOR SEQ ID NO:16:

( i ) SEQUENCE CHARACTERISTICS:
        ( A ) LENGTH: 79 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
GGGAGAUGCC UGUCGAGCAU GCUGGGUAAC GCUGUGGACA AGUGCACCAG            50

CUGCGUAGCU AAACAGCUUU GUCGACGGG                                    79
```

( 2 ) INFORMATION FOR SEQ ID NO:17:

( i ) SEQUENCE CHARACTERISTICS:
        ( A ) LENGTH: 79 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
GGGAGAUGCC UGUCGAGCAU GCUGAGGGUA ACGUACUGGC AAGCUCACCU            50

CAGCGUAGCU AAACAGCUUU GUCGACGGG                                    79
```

( 2 ) INFORMATION FOR SEQ ID NO:18:

( i ) SEQUENCE CHARACTERISTICS:
        ( A ) LENGTH: 79 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
GGGAGAUGCC UGUCGAGCAU GCUGAGGGUA ACGUAUAGUC AAGACACCUC            50

AAGUGUAGCU AAACAGCUUU GUCGACGGG                                    79
```

( 2 ) INFORMATION FOR SEQ ID NO:19:

( i ) SEQUENCE CHARACTERISTICS:
        ( A ) LENGTH: 79 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
GGGAGAUGCC UGUCGAGCAU GCUGGGGUAA CGCAUUGGCA AGACACCCAG            50

CCCCGUAGCU AAACAGCUUU GUCGACGGG                                    79
```

( 2 ) INFORMATION FOR SEQ ID NO:20:

( i ) SEQUENCE CHARACTERISTICS:
        ( A ) LENGTH: 79 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:20:

```
GGGAGAUGCC UGUCGAGCAU GCUGGAGGAA ACGUACCGUC GAGCCACUCC            50

AUGCGUAGCU AAACAGCUUU GUCGACGGG                                    79
```

( 2 ) INFORMATION FOR SEQ ID NO:21:

( i ) SEQUENCE CHARACTERISTICS:
        ( A ) LENGTH: 79 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
GGGAGAUGCC  UGUCGAGCAU  GCUGGGGUAA  CGUGUGACAA  GAUCACCCAG         50

UUUGGUAGCU  AAACAGCUUU  GUCGACGGG                                  79
```

( 2 ) INFORMATION FOR SEQ ID NO:22:

( i ) SEQUENCE CHARACTERISTICS:
        ( A ) LENGTH: 79 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
GGGAGAUGCC  UGUCGAGCAU  GCUGCACAGG  GCAACGCUGC  UGACAAGUGC         50

ACCUGUAGCU  AAACAGCUUU  GUCGACGGG                                  79
```

( 2 ) INFORMATION FOR SEQ ID NO:23:

( i ) SEQUENCE CHARACTERISTICS:
        ( A ) LENGTH: 28 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
NNNGGUAACG  NNNNGNCAAG  UACACNNN                                   28
```

( 2 ) INFORMATION FOR SEQ ID NO:24:

( i ) SEQUENCE CHARACTERISTICS:
        ( A ) LENGTH: 16 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
NGCUAACCAG  GACACN                                                 16
```

( 2 ) INFORMATION FOR SEQ ID NO:25:

( i ) SEQUENCE CHARACTERISTICS:
        ( A ) LENGTH: 45 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:25:

```
UGACUCGAAC  CCUUGGAAGA  CCUGAGUACA  GGUAUACCAG  UUCGA              45
```

( 2 ) INFORMATION FOR SEQ ID NO:26:

( i ) SEQUENCE CHARACTERISTICS:
        ( A ) LENGTH: 47 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:26:

CGCUCAAUCC UUGGAAGCCG UACGGAUACC AAUUGAGUGG CCAUAUG 47

( 2 ) INFORMATION FOR SEQ ID NO:27:

( i ) SEQUENCE CHARACTERISTICS:
        ( A ) LENGTH: 40 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:27:

UAUCGAGUGG CCUUGGCAGA CCAGGCCGG UAUACCACCA 40

( 2 ) INFORMATION FOR SEQ ID NO:28:

( i ) SEQUENCE CHARACTERISTICS:
        ( A ) LENGTH: 40 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:28:

CGAGAUUCAA CCUUGGAAGU CAAUCGUGAA UACCAUUGUU 40

( 2 ) INFORMATION FOR SEQ ID NO:29:

( i ) SEQUENCE CHARACTERISTICS:
        ( A ) LENGTH: 32 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:29:

NNNCCUUGGA CAGNNNNNNN NNNAUACCAN NN 32

( 2 ) INFORMATION FOR SEQ ID NO:30:

( i ) SEQUENCE CHARACTERISTICS:
        ( A ) LENGTH: 37 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:30:

UCAAGAAUUC CGUUUUCAGU CGGGAAAAAC UGAACAA 37

( 2 ) INFORMATION FOR SEQ ID NO:31:

( i ) SEQUENCE CHARACTERISTICS:
        ( A ) LENGTH: 37 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:31:

GAAUAUCUUC CGAAGCCGAA CGGGAAAACC GGCAUCU 37

( 2 ) INFORMATION FOR SEQ ID NO:32:

( i ) SEQUENCE CHARACTERISTICS:
        ( A ) LENGTH: 34 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:32:

UCAAGGUUUC CGAAAGAAAU CGGGAAAACU GUCU 34

( 2 ) INFORMATION FOR SEQ ID NO:33:

( i ) SEQUENCE CHARACTERISTICS:
        ( A ) LENGTH: 37 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:33:

AGUAGAUAUC CGAAGCUCAA CGGGAUAAUG AGCAUCU        37

( 2 ) INFORMATION FOR SEQ ID NO:34:

( i ) SEQUENCE CHARACTERISTICS:
        ( A ) LENGTH: 36 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:34:

AGAUAUGAUC CGUAAGAGGA CGGGAUAAAC CUCAAC        36

( 2 ) INFORMATION FOR SEQ ID NO:35:

( i ) SEQUENCE CHARACTERISTICS:
        ( A ) LENGTH: 37 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:35:

GUCAUAUUAC CGUUACUCCU CGGGAUAAAG GAGAUCU        37

( 2 ) INFORMATION FOR SEQ ID NO:36:

( i ) SEQUENCE CHARACTERISTICS:
        ( A ) LENGTH: 37 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:36:

AGGAAUCGAC CCAAGCCAAA GGGGAUAAUG CGGCAUC        37

( 2 ) INFORMATION FOR SEQ ID NO:37:

( i ) SEQUENCE CHARACTERISTICS:
        ( A ) LENGTH: 37 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:37:

AGUAAUGACC AGAGGCCAA CUGGUAAACG GGCGGUC        37

( 2 ) INFORMATION FOR SEQ ID NO:38:

( i ) SEQUENCE CHARACTERISTICS:
        ( A ) LENGTH: 26 BASE PAIRS
        ( B ) TYPE: nucleic acid
        ( C ) STRANDEDNESS: single
        ( D ) TOPOLOGY: linear ( x i ) SEQUENCE DESCRIPTION: SEQ ID NO:38:

UCCGNNNNNN NNNCGGGANA ANNNNN        26

( 2 ) INFORMATION FOR SEQ ID NO:39:

( i ) SEQUENCE CHARACTERISTICS:
  ( A ) LENGTH: 39 BASE PAIRS
  ( B ) TYPE: nucleic acid
  ( C ) STRANDEDNESS: single
  ( D ) TOPOLOGY: linear ( x i ) SEQUENCE DESCRIPTION: SEQ ID NO:39:

GAAUGAAUGU GAUGAACAGG UGUCGGGGUG GAUGGGUGG  39

( 2 ) INFORMATION FOR SEQ ID NO:40:

( i ) SEQUENCE CHARACTERISTICS:
  ( A ) LENGTH: 40 BASE PAIRS
  ( B ) TYPE: nucleic acid
  ( C ) STRANDEDNESS: single
  ( D ) TOPOLOGY: linear ( x i ) SEQUENCE DESCRIPTION: SEQ ID NO:40:

GGAAUGAAUG UGAUGAACAG GUGUCGGGGU GGAUGGGUGG  40

( 2 ) INFORMATION FOR SEQ ID NO:41:

( i ) SEQUENCE CHARACTERISTICS:
  ( A ) LENGTH: 40 BASE PAIRS
  ( B ) TYPE: nucleic acid
  ( C ) STRANDEDNESS: single
  ( D ) TOPOLOGY: linear ( x i ) SEQUENCE DESCRIPTION: SEQ ID NO:41:

AGAAUGAAUG UGAUGAACAG GUGUCGGGGU GGAUGGGUGG  40

( 2 ) INFORMATION FOR SEQ ID NO:42:

( i ) SEQUENCE CHARACTERISTICS:
  ( A ) LENGTH: 40 BASE PAIRS
  ( B ) TYPE: nucleic acid
  ( C ) STRANDEDNESS: single
  ( D ) TOPOLOGY: linear ( x i ) SEQUENCE DESCRIPTION: SEQ ID NO:42:

CGCCUUAGUC GCCAUAAUGC UGUCGGGGUG GAUAGGUGG  40

( 2 ) INFORMATION FOR SEQ ID NO:43:

( i ) SEQUENCE CHARACTERISTICS:
  ( A ) LENGTH: 40 BASE PAIRS
  ( B ) TYPE: nucleic acid
  ( C ) STRANDEDNESS: single
  ( D ) TOPOLOGY: linear ( x i ) SEQUENCE DESCRIPTION: SEQ ID NO:43:

GACGCGUGCU GGCCUCGACC GUGUGGGUGC GGAUGGGUGG  40

( 2 ) INFORMATION FOR SEQ ID NO:44:

( i ) SEQUENCE CHARACTERISTICS:
  ( A ) LENGTH: 15 BASE PAIRS
  ( B ) TYPE: nucleic acid
  ( C ) STRANDEDNESS: single
  ( D ) TOPOLOGY: linear ( x i ) SEQUENCE DESCRIPTION: SEQ ID NO:44:

GGGGUGGAUG GGUGG  15